United States Patent
Sakarya et al.

(10) Patent No.: US 12,006,533 B2
(45) Date of Patent: Jun. 11, 2024

(54) DETECTING CROSS-CONTAMINATION IN SEQUENCING DATA USING REGRESSION TECHNIQUES

(71) Applicant: Grail, Inc., Menlo Park, CA (US)

(72) Inventors: Onur Sakarya, San Francisco, CA (US); Catalin Barbacioru, Fremont, CA (US)

(73) Assignee: GRAIL, LLC, Menlo Park, CA (US)

( * ) Notice: Subject to any disclaimer, the term of this patent is extended or adjusted under 35 U.S.C. 154(b) by 751 days.

(21) Appl. No.: 15/900,645

(22) Filed: Feb. 20, 2018

(65) Prior Publication Data
US 2018/0237838 A1 Aug. 23, 2018

Related U.S. Application Data

(63) Continuation of application No. PCT/IB2018/050979, filed on Feb. 17, 2018.

(60) Provisional application No. 62/525,653, filed on Jun. 27, 2017, provisional application No. 62/460,268, filed on Feb. 17, 2017.

(51) Int. Cl.
| | | |
|---|---|---|
| *C12Q 1/6827* | (2018.01) | |
| *C12Q 1/6809* | (2018.01) | |
| *G16B 20/20* | (2019.01) | |
| *G16B 30/10* | (2019.01) | |
| *G16B 30/20* | (2019.01) | |
| *G16B 40/20* | (2019.01) | |
| *G16B 40/30* | (2019.01) | |

(52) U.S. Cl.
CPC ......... *C12Q 1/6827* (2013.01); *C12Q 1/6809* (2013.01); *G16B 20/20* (2019.02); *G16B 30/10* (2019.02); *G16B 40/20* (2019.02); *G16B 40/30* (2019.02); *G16B 30/20* (2019.02)

(58) Field of Classification Search
CPC .............................. G16B 20/20; G16B 40/20
See application file for complete search history.

(56) References Cited

U.S. PATENT DOCUMENTS

| | | | | |
|---|---|---|---|---|
| 2012/0264121 A1* | 10/2012 | Rava | ..................... | C12Q 1/6876 435/6.11 |
| 2014/0127688 A1* | 5/2014 | Umbarger | ............ | C12Q 1/6881 435/6.11 |
| 2018/0237838 A1 | 8/2018 | Sakarya et al. | | |
| 2018/0373832 A1 | 12/2018 | Sakarya et al. | | |

FOREIGN PATENT DOCUMENTS

| | | |
|---|---|---|
| AU | 2015205935 A1 | 8/2015 |
| WO | WO 2013/028699 A2 | 2/2013 |
| WO | WO 2014/074611 A1 | 5/2014 |
| WO | WO 2016/115307 A1 | 7/2016 |
| WO | WO 2018/150378 A1 | 8/2018 |

OTHER PUBLICATIONS

Xu et al., Detecting very low allele fraction variants using targeted DNA sequencing and a novel molecular barcode-aware variant caller, 2017, BMC Genomics, 18(5), p. 1-11 (Year: 2017).*
Bergmann et al., Conpair: concordance and contamination estimator for matched tumor-normal pairs, 2016, Bioinformatics, 32(2), p. 3196-3198 (Year: 2016).*
Surdhar, Cycle Sequencing of PCR Products, 2002, PCR Mutation Detection Protocols. Methods in Molecular Biology, 187, p. 65-72 (Year: 2002).*
Ignatiadis et al., Circulating Tumor Cells and Circulating Tumor DNA: Challenges and Opportunities on the Path to Clinical Utility, 2015, Clin Cancer Res, 21(21), p. 4786-4800 (Year: 2015).*
PCT International Search Report and Written Opinion, PCT Application No. PCT/US2018/039609, dated Sep. 28, 2018, 17 pages.
Theunert, C. et al., "Joint Estimation of Relatedness Coefficients and Allele Frequencies from Ancient Samples," Genetics, vol. 206, No. 2, Jun. 7, 2017, pp. 1025-1035.
Bergmann, et al., "Conpair: concordance and contamination estimator for matched tumor-normal pairs," Bioinformatics 32(20), pp. 3196-3198 (2016).
Cibulskis, K. et al., "ContEst: Estimating Cross-Contamination of Human Samples in Next-Generation Sequencing Data," Bioinformatics, Jul. 29, 2011, pp. 2601-2602, vol. 27, No. 18.
Jun, G. et al., "Detecting and Estimating Contamination of Human DNA Samples in Sequencing and Array-Based Genotype Data," The American Journal of Human Genetics, Nov. 2, 2012, pp. 839-848, vol. 91, No. 5.
Kim, S. et al., "Virmid: Accurate Detection of Somatic Mutations with Sample Impurity Inference," Genome Biology, Biomed Central Ltd., Aug. 29, 2013, 17 pages, R90, vol. 14, No. 8.
PCT International Search Report and Written Opinion, PCT Application No. PCT/IB2018/050979, dated Apr. 18, 2018, 16 pages.
Sakarya, O. et al., "Conta: methods for detecting trace amounts of contamination," Poster, ISMB conference, (Jul. 21-24, 2017).

(Continued)

*Primary Examiner* — Kaitlyn L Minchella
(74) *Attorney, Agent, or Firm* — Fenwick & West LLP

(57) ABSTRACT

Cross-contamination of a test sample used to determine cancer is identified using gene sequencing data. Each test sample includes a number of test sequences that may include a single nucleotide polymorphism (SNP) that can be indicative of cancer. The test sequences are be filtered to remove or negate at least some of the SNPs from the test sequences. Negating the test sequences allows more test sequences to be simultaneously analyzed to determine cross-contamination. Cross-contamination is determined by modeling the variant allele frequency for the test sequences as a function of minor allele frequency, contamination level, and background noise. In some cases, the variant allele frequency is based on a probability function including the minor allele frequency. Cross-contamination of the test sample is determined if the determined contamination level is above a threshold and statistically significant.

14 Claims, 40 Drawing Sheets

(56) References Cited

OTHER PUBLICATIONS

PCT International Search Report and Written Opinion, PCT Application No. PCT/US2021/050995, dated Mar. 3, 2022, 21 pages.
PCT Invitation to Pay Additional Fees, PCT Application No. PCT/US2021/050995, dated Jan. 10, 2022, 15 pages.
Shiraishi, M. et al. "High-Speed Conversion of Cytosine to Uracil in Bisulfite Genomic Sequencing Analysis of DNA Methylation." DNA Research, vol. 11, No. 6, Dec. 1, 2004, pp. 409-415.
Flickinger et al., "Detecting and Correcting Contamination in Genetic Data," Doctoral dissertation, 2016, p. 1-90.
Karoui, N. E. et al., "Getting more from digital SNP data," Statistics in medicine 25.18, Sep. 30, 2006, pp. 3124-3133.
Eisenberg, "Sequential probability ratio test," Encyclopedia of Mathematics, 2011, pp. 1-3.
Stanford, "Introduction to Statistical Inference—Bayesian Analysis," 2016, pp. 20-21 to 20-4.
United States Office Action, U.S. Appl. No. 16/019,315, dated Jun. 9, 2023, 46 pages.
United States Office Action, U.S. Appl. No. 16/019,315, dated Nov. 18, 2022, 52 pages.
United States Office Action, U.S. Appl. No. 16/019,315, dated Nov. 7, 2023, 24 pages.
United States Office Action, U.S. Appl. No. 16/019,315, filed Apr. 18, 2024, 19 pages.

* cited by examiner

VAF Distribution Plot 1330

VAF Distribution Plot 1340

Kernel density plot 2540

Kernel density plot 2550

DETECTING CROSS-CONTAMINATION IN SEQUENCING DATA USING REGRESSION TECHNIQUES

CROSS REFERENCE TO RELATED APPLICATIONS

This application is a continuation of International Application No. PCT/IB2018/050979 filed Feb. 17, 2018; which claims the benefit of priority to U.S. Provisional Application No. 62/460,268, filed Feb. 17, 2017 and U.S. Provisional Application No. 62/525,653, filed Jun. 27, 2017, all of which are incorporated herein by reference in their entirety for all purposes

BACKGROUND

1. Field of Art

This application relates generally to detecting contamination in a sample, and more specifically to detecting contamination in a sample including targeted sequencing used for early detection of cancer.

2. Description of the Related Art

Next generation sequencing-based assays of circulating tumor DNA must achieve high sensitivity and specificity in order to detect cancer early. Early cancer detection and liquid biopsy both require highly sensitive methods to detect low tumor burden as well as specific methods to reduce false positive calls. Contaminating DNA from adjacent samples can compromise specificity which can result in false positive calls. In various instances, compromised specificity can be because rare SNPs from the contaminant may look like low level mutations. Methods currently exist for detecting and estimating contamination in whole genome sequencing data, typically from relatively low-depth sequencing studies. However, existing methods are not designed for detection of contamination in sequencing data from cancer detection samples, which typically require high-depth sequencing studies and include tumor-derived mutations (e.g., single base mutations and/or copy number variations (CNVs)) that may be present at varying frequencies (e.g., clonal and/or sub-clonal tumor-derived mutations). There is a need for new methods of detecting cross-sample contamination in sequencing data from a test sample used for cancer detection.

SUMMARY

Embodiments described herein relate to methods of analyzing sequencing data to detect cross-sample contamination in a test sample. Determining cross-contamination in a test sample can be informative for determining that the test sample will be less likely to correctly identify the presence of cancer in the subject. In one example, cross-contamination is determined in a nucleic acid sample obtained from a human subject and used for the early detection of cancer.

In various embodiments, test samples are obtained from subjects and prepared using genome sequencing techniques. Each test sample includes a number of test sequences including at least one single nucleotide polymorphism that can be indicative of cancer. The test sequences can be filtered to remove or negate at least some of the SNPs from the test sequences based on a variety of criteria. In one example, test sequences that are heterozygous are removed while test sequences that are homozygous alternative alleles are negated. Negating a test sequence modifies the data of the test sequence such that it can be more easily analyzed to determine cross-contamination.

Generally, SNPs of the test sample at a given site are expected to have a variant allele frequency that can be modeled as a function of the minor allele frequency for SNPs at that site in a population, a contamination level, and a noise level. In some cases, the model can include a probability function based on the minor allele frequencies. Therefore, when analyzing the test sample obtained from a subject, variations from the expected variant allele frequency can be determined utilizing regression modeling. Specifically, regression modeling can be used to determine a contamination level and its statistical significance based on the relationship between the variant allele frequency and the minor allele frequency for a given site. If the determined contamination level of the test sample is above a threshold contamination level and the determined contamination level is statistically significant, a contamination event can be called. Calling a contamination event can indicate that at least some sequences included in the test sample originate from a different subject.

Figure 1:
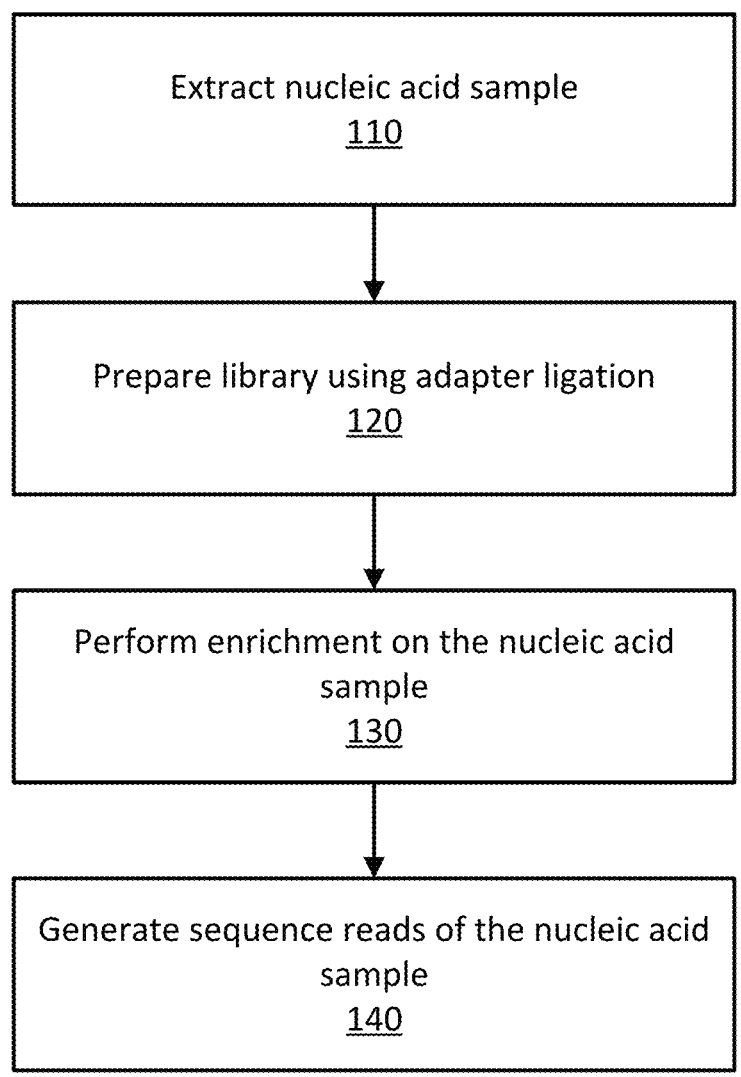
FIG. 1 is a flowchart of a method for preparing a nucleic acid sample for sequencing, according to one example embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Definitions

The term "individual" refers to a human individual. The term "healthy individual" refers to an individual presumed to not have cancer or disease. The term "subject" refers to an individual who is known to have, or potentially has, cancer or disease.

The term "sequence reads" refers to nucleotide sequences read from a sample obtained from an individual. Sequence reads can be obtained through various methods known in the art.

The term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

The term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

The term "single nucleotide polymorphism" or "SNP" refers to a substitution of one nucleotide to a different nucleotide at a position (e.g., site) of a nucleotide sequence, e.g., a sequence read from an individual. For example, at a specific base site, the nucleobase C may appear in most individuals, but in a minority of individuals, the position is occupied by base A. There is a SNP at this specific site.

The term "indel" refers to any insertion or deletion of one or more base pairs having a length and a position (which may also be referred to as an anchor position) in a sequence read. An insertion corresponds to a positive length, while a deletion corresponds to a negative length.

The term "mutation" refers to one or more SNVs or indels.

The term "true positive" refers to a mutation that indicates real biology, for example, the presence of potential cancer, disease, or germline mutation in an individual. True positives are not caused by mutations naturally occurring in healthy individuals (e.g., recurrent mutations) or other sources of artifacts such as process errors during assay preparation of nucleic acid samples.

The term "false positive" refers to a mutation incorrectly determined to be a true positive. Generally, false positives may be more likely to occur when processing sequence reads associated with greater mean noise rates or greater uncertainty in noise rates.

The term "cell-free nucleic acid," "cell-free DNA," "cfDNA," "cell-free RNA," or "cfRNA" refers to nucleic acid fragments that circulate in an individual's body (e.g., bloodstream) and originate from one or more healthy cells and/or from one or more cancer cells.

The term "circulating tumor DNA" or "ctDNA" refers to nucleic acid fragments that originate from tumor cells or other types of cancer cells, which may be released into an individual's bloodstream as result of biological processes such as apoptosis or necrosis of dying cells or actively released by viable tumor cells.

The term "genomic nucleic acid," "genomic DNA," or "gDNA" refers to nucleic acid including chromosomal DNA that originates from one or more healthy cells.

The term "alternative allele" or "ALT" refers to an allele having one or more mutations relative to a reference allele, e.g., corresponding to a known gene.

The term "minor allele" or "MIN" refers to the second most common allele in a given population.

The term "sequencing depth" or "depth" refers to a total number of read segments from a sample obtained from an individual that have a particular location in the genome.

The term "allele depth" or "AD" refers to a number of read segments in a sample that supports an allele in a population. The terms "AAD", "MAD" refer to the "alternate allele depth" (i.e., the number of read segments that support an ALT) and "minor allele depth" (i.e., the number of read segments that support a MIN), respectively.

The term "contaminated" refers to a test sample that is contaminated with at least some portion of a second test sample. That is, a contaminated test sample unintentionally includes DNA sequences from an individual that did not generate the test sample. Similarly, the term "uncontaminated" refers to a test sample that does not include at least some portion of a second test sample.

The term "contamination level" refers to the degree of contamination in a test sample. That is, the contamination level the number of reads in a first test sample from a second test sample. For example, if a first test sample of 1000 reads includes 30 reads from a second test sample, the contamination level is 3.0%.

The term "contamination event" refers to a test sample being called contaminated. Generally, a test sample is called contaminated if the determined contamination level is above a threshold contamination level and the determined contamination level is statistically significant.

The term "allele frequency" or "AF" refers to the frequency of a given allele in a population. The terms "AAF", "MAF" refer to the "alternate allele frequency" and "minor allele frequency", respectively. Herein, the term "variant allele frequency" refers to the minor allele frequency for an allele of the test sample. In this case, the VAF may be determined by dividing the corresponding variant allele depth of a test sample by the total depth of the sample for the given allele.

II. Example Assay Protocol

FIG. 1 is a flowchart of a method 100 for preparing a nucleic acid sample for sequencing according to one embodiment. The method 100 includes, but is not limited to, the following steps. For example, any step of the method 100 may comprise a quantitation sub-step for quality control or other laboratory assay procedures known to one skilled in the art.

In step 110, a nucleic acid sample (DNA or RNA) is extracted from a subject. In the present disclosure, DNA and RNA may be used interchangeably unless otherwise indicated. That is, the following embodiments for using error source information in variant calling and quality control may be applicable to both DNA and RNA types of nucleic acid sequences. However, the examples described herein may focus on DNA for purposes of clarity and explanation. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has cancer or disease, ctDNA in an extracted sample may be present at a detectable level for diagnosis.

In step 120, a sequencing library is prepared. During library preparation, unique molecular identifiers (UMI) are added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment, which provides a way to identify sequence reads that came from the same original fragment in downstream analysis.

In step 130, targeted DNA sequences are enriched from the library. During enrichment, hybridization probes (also referred to herein as "probes") are used to target, and pull down, nucleic acid fragments informative for the presence or absence of cancer (or disease), cancer status, or a cancer classification (e.g., cancer type or tissue of origin). For a given workflow, the probes may be designed to anneal (or hybridize) to a target (complementary) strand of DNA or RNA. The target strand may be the "positive" strand (e.g., the strand transcribed into mRNA, and subsequently translated into a protein) or the complementary "negative" strand. The probes may range in length from 10s, 100s, or 1000s of base pairs. In one embodiment, the probes are designed based on a gene panel to analyze particular mutations or target regions of the genome (e.g., of the human or another organism) that are suspected to correspond to certain cancers or other types of diseases. Moreover, the probes may cover overlapping portions of a target region. By using a targeted gene panel rather than sequencing all expressed genes of a genome, also known as "whole exome sequencing," the method 100 may be used to increase sequencing depth of the target regions, where depth refers to the count of the number of times a given target sequence within the sample has been sequenced. Increasing sequencing depth reduces required input amounts of the nucleic acid sample. After a hybridization step, the hybridized nucleic acid fragments are captured and may also be amplified using PCR.

In step 140, sequence reads are generated from the enriched DNA sequences. Sequencing data may be acquired from the enriched DNA sequences by known means in the art. For example, the method 100 may include next-generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary) format may be generated and output for further analysis such as variant calling, as described below with respect to FIG. 2.

III. Example Processing System

Figure 2:
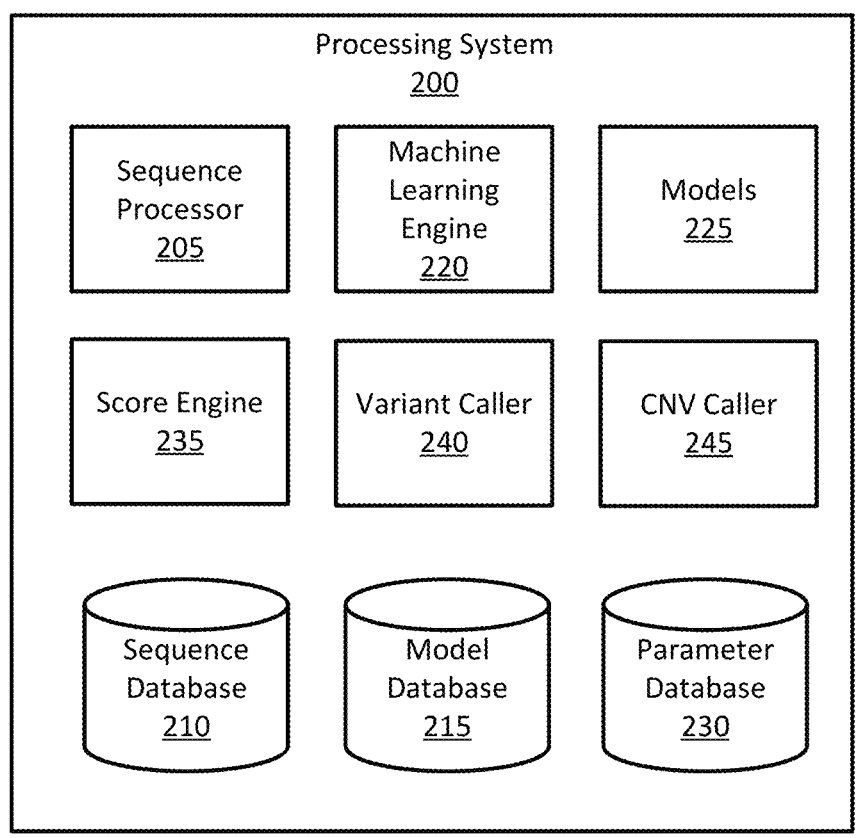
FIG. 2 is a block diagram of a processing system for processing sequence reads, according to one example embodiment.
Figure 3:
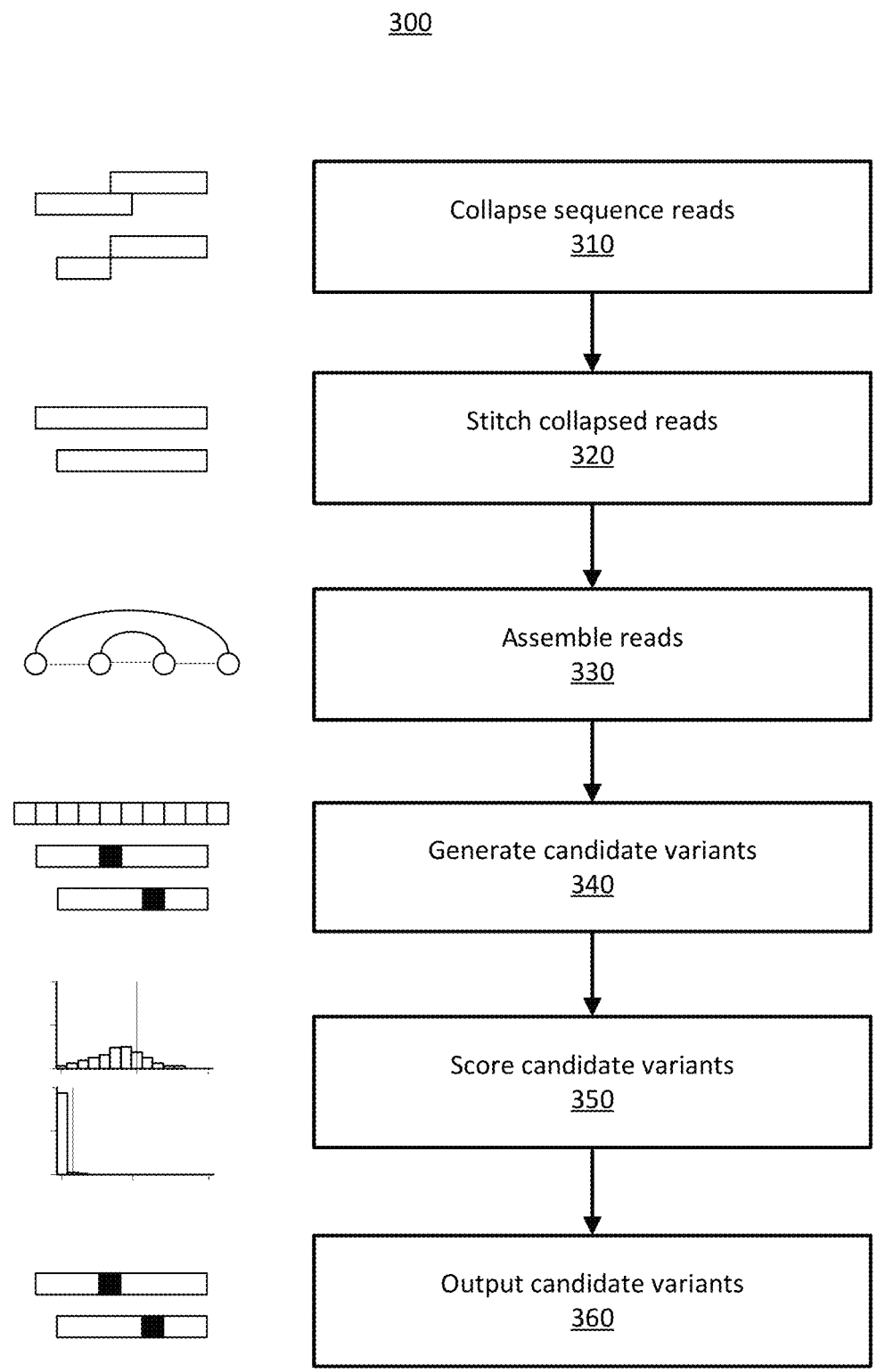
FIG. 3 is a flowchart of a method for determining variants of sequence reads, according to one example embodiment.

FIG. 2 is a block diagram of a processing system 200 for processing sequence reads, according to one example embodiment. The processing system 200 includes a sequence processor 205, sequence database 210, model database 215, machine learning engine 220, models 225, parameter database 230, score engine 235, variant caller 240 and copy number variation (CNV) caller 245. FIG. 3 is a flowchart of a method 300 for determining variants of sequence reads, according to one example embodiment. In some embodiments, the processing system 200 performs the method 300 to perform variant calling (e.g., for SNPs) based on input sequencing data. Further, the processing system 200 may obtain the input sequencing data from an output file associated with a nucleic acid sample prepared using the method 100 described above. The method 300 includes, but is not limited to, the following steps, which are described with respect to the components of the processing system 200. In other embodiments, one or more steps of the method 300 may be replaced by a step of a different process for generating variant calls, e.g., using Variant Call Format (VCF), such as HaplotypeCaller, VarScan, Strelka, or SomaticSniper.

The processing system 200 can be any type of computing device that is capable of running program instructions. Examples of processing system 200 may include, but are not limited to, a desktop computer, a laptop computer, a tablet device, a personal digital assistant (PDA), a mobile phone or smartphone, and the like. In one example, when processing system is a desktop or laptop computer, models 225 may be executed by a desktop application. Applications can, in other examples, be a mobile application or web-based application configured to execute the models 225.

At step 310, the sequence processor 205 collapses aligned sequence reads of the input sequencing data. In one embodiment, collapsing sequence reads includes using UMIs, and optionally alignment position information from sequencing data of an output file (e.g., from the method 100 shown in FIG. 1) to collapse multiple sequence reads into a consensus sequence for determining the most likely sequence of a nucleic acid fragment or a portion thereof. Since the UMIs are replicated with the ligated nucleic acid fragments through enrichment and PCR, the sequence processor 205 may determine that certain sequence reads originated from the same molecule in a nucleic acid sample. In some embodiments, sequence reads that have the same or similar alignment position information (e.g., beginning and end positions within a threshold offset) and include a common UMI are collapsed, and the sequence processor 205 generates a collapsed read (also referred to herein as a consensus read) to represent the nucleic acid fragment. The sequence processor 205 designates a consensus read as "duplex" if the corresponding pair of collapsed reads have a common UMI, which indicates that both positive and negative strands of the originating nucleic acid molecule are captured; otherwise, the collapsed read is designated "non-duplex." In some embodiments, the sequence processor 205 may perform other types of error correction on sequence reads as an alternative to, or in addition to, collapsing sequence reads.

At step 320, the sequence processor 205 stitches the collapsed reads based on the corresponding alignment position information. In some embodiments, the sequence processor 205 compares alignment position information between a first read and a second read to determine whether nucleotide base pairs of the first and second reads overlap in the reference genome. In one use case, responsive to determining that an overlap (e.g., of a given number of nucleotide bases) between the first and second reads is greater than a threshold length (e.g., threshold number of nucleotide bases), the sequence processor 205 designates the first and second reads as "stitched"; otherwise, the collapsed reads are designated "unstitched." In some embodiments, a first and second read are stitched if the overlap is greater than the threshold length and if the overlap is not a sliding overlap. For example, a sliding overlap may include a homopolymer run (e.g., a single repeating nucleotide base), a dinucleotide run (e.g., two-nucleotide base sequence), or a trinucleotide run (e.g., three-nucleotide base sequence), where the homopolymer run, dinucleotide run, or trinucleotide run has at least a threshold length of base pairs.

At step 330, the sequence processor 205 assembles reads into paths. In some embodiments, the sequence processor 205 assembles reads to generate a directed graph, for example, a de Bruijn graph, for a target region (e.g., a gene). Unidirectional edges of the directed graph represent sequences of k nucleotide bases (also referred to herein as "k-mers") in the target region, and the edges are connected by vertices (or nodes). The sequence processor 205 aligns collapsed reads to a directed graph such that any of the collapsed reads may be represented in order by a subset of the edges and corresponding vertices.

At step 340, the variant caller 240 generates candidate variants from the paths assembled by the sequence processor 205. In one embodiment, the variant caller 240 generates the candidate variants by comparing a directed graph (which may have been compressed by pruning edges or nodes in step 310) to a reference sequence of a target region of a genome. The variant caller 240 may align edges of the directed graph to the reference sequence, and records the genomic positions of mismatched edges and mismatched nucleotide bases adjacent to the edges as the locations of candidate variants. Additionally, the variant caller 240 may generate candidate variants based on the sequencing depth of a target region. In particular, the variant caller 240 may be more confident in identifying variants in target regions that have greater sequencing depth, for example, because a greater number of sequence reads help to resolve (e.g., using redundancies) mismatches or other base pair variations between sequences. In some embodiments, the variants can be SNPs.

Further, multiple different models may be stored in the model database 215 or retrieved for application post-training. For example, models may be trained to determine the presence of a contamination event (e.g., contamination of a test sample during process 100 or process 300) and/or verify contamination detection. Further, the score engine 235 may use parameters of the model 225 to determine a likelihood of one or more true positives or contamination in a sequence read. The score engine 235 may determine a quality score (e.g., on a logarithmic scale) based on the likelihood. For example, the quality score is a Phred quality score $Q = -10 \cdot \log_{10} P$, where P is the likelihood of an incorrect candidate variant call (e.g., a false positive). In some embodiments, CNV caller 245 can call copy number variations using a model stored in the model database 215. In one example, CNVs can associated with cancer care identified using a model that analyzes random sequencing data. In another example, CNVs associated with cancer are identified using a model that analyzes allele ratios at a plurality of heterozygous loci within a region of the genome.

At step 350, the score engine 235 scores the candidate variants based on the model 225 or corresponding likelihoods of true positives, contamination, quality scores, etc. Training and application of the model 225 are described in more detail below.

At step 360, the processing system 200 outputs the candidate variants. In some embodiments, the processing system 200 outputs some or all of the determined candidate variants along with the corresponding scores. Downstream systems, e.g., external to the processing system 200 or other components of the processing system 200, may use the candidate variants and scores for various applications including, but not limited to, predicting the presence of cancer, predicting contamination in test sequences, predicting noise levels, or germline mutations.

IV. Example Contamination Detection Workflow

Figure 4:
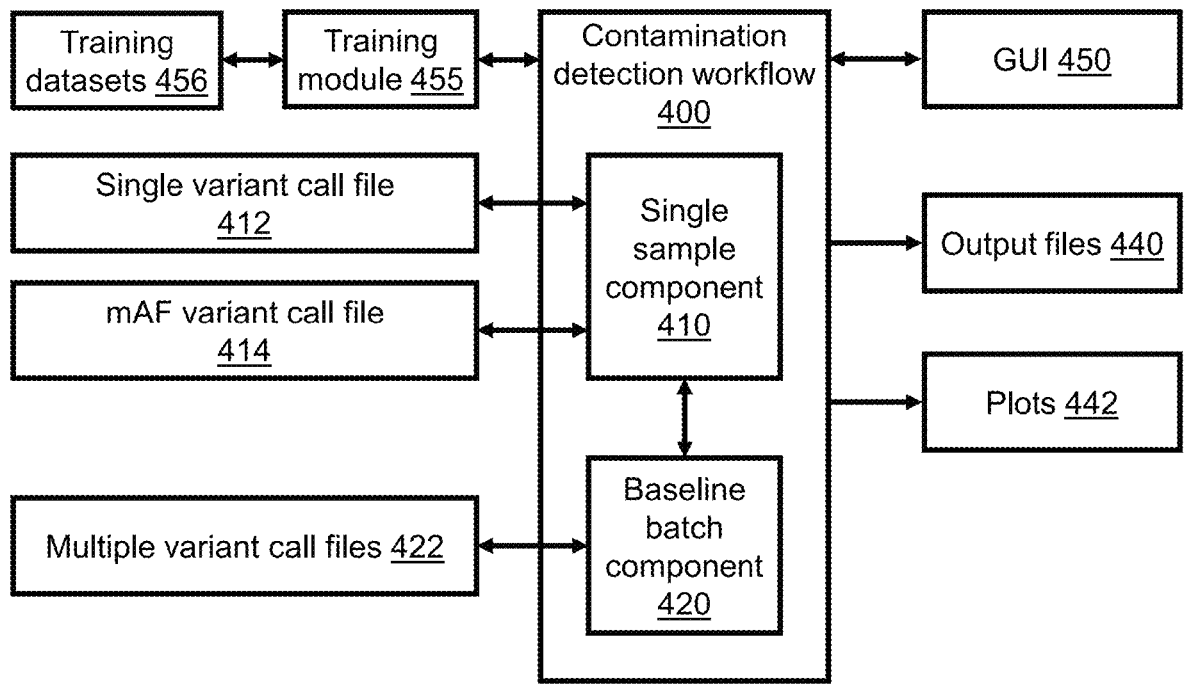
FIG. 4 illustrates a block diagram of a contamination detection workflow for detecting and calling contamination in a test sample, according to one example embodiment.

FIG. 4 is a diagram of a contamination detection workflow 400 executing on the processing system 200 for detecting and calling contamination, in accordance with one embodiment.

In the illustrated example, contamination detection workflow 400 includes a single sample component 410 and a baseline batch component 420. Single sample component 410 of contamination detection workflow 400 is informed, for example, by the contents of a single variant call file 442 and a minor allele frequencies (MAF) variant call file 444 called by the variant caller 240. The single variant call file 442 is the variant call file for a single target sample. The MAF variant call file 444 is the MAF variant call file for any number of SNP population allele frequencies AF.

Baseline batch component 420 of contamination detection workflow 400 generates a background noise baseline for each SNP from uncontaminated samples as another input to single sample component 410. Generating a background noise baseline is described in more detail below. Baseline batch component 420 is informed, for example, by the contents of multiple variant call files 422 called by the variant caller 240. The multiple variant call files 422 can be the variant call files of multiple samples and are, in some examples, variants that are determined to be healthy samples. Healthy samples are samples previously determined not to include cancer.

In one embodiment, the contamination detection workflow 400 can generate output files 440 and/or plots from sequencing data processed by contamination detection algorithm 110. For example, contamination detection workflow 400 may generate variant allele frequency distribution plots or regression plots as a means for evaluating a DNA test sample for contamination. Data processed by contamination detection workflow 400 can be visually presented to the user via a graphical user interface (GUI) 450 of the processing system 200. For example, the contents of output files 440 (e.g., a text file of data opened in Excel) and regression plots, for example, can be displayed in GUI 450. In an additional example, the contamination detection workflow 400 can discard a sample if a contamination call is made (e.g., identifying a contamination event). In this case, one or more additional aliquots (e.g., test sequences) from the original sample can then be processed (because they are, e.g., uncontaminated).

In another embodiment, the contamination detection workflow 400 may use the machine learning engine 220 to improve contamination detection. Various training datasets (e.g., parameters from parameter database 230, sequences from sequence database 210, etc.) may be used to supply information to the machine learning engine 220 as described herein. In accordance with this embodiment, the machine learning engine 220 may be used to train a contamination noise baseline to identify a noise threshold, determine a contamination level, determine a contamination event, and determine the limit of detection (LOD) for contamination detection. Additionally, machine learning engine may be used to calculate the sensitivity (true positive rate) and specificity (true negative rate) for contamination detection. That is, machine learning engine 220 can analyze different statistical significance indicators (such as p-values) and determine the threshold that achieves highest sensitivity at the minimum desired specificity level (e.g. 99%) for determining a contamination event.

Single sample component 410 of contamination detection workflow 400 is, for example, a runnable script that is used to estimate contamination in a sample. By contrast, baseline batch component 430 of contamination detection algorithm 110 is, for example, a runnable script that is used for generating estimates across a batch of samples, and may also be used to generate a background noise model across these samples. The noise model is generated from a batch of samples previously determined to be healthy.

V. Detecting Contamination Using MAF and Noise

In one embodiment, the contamination detection workflow 400 may be based on a model for estimating contamination. In one example, the model is a linear regression model based on population minor allele frequencies, herein referred to as the "population model" for clarity, that is configured for detecting contamination in sequencing data from a test sample.

In one example, the population model determines contamination by calculating a probability that the observed variant frequency VAF for a test sample is statistically significant relative to the population minor allele frequency MAF and a background noise baseline. That is, the population model calculates a probability of observing a variant allele frequency VAF of a test sample at a given contamination level $\alpha$ of the average minor allele frequency MAF of the population. If the population model determines that the observed VAF for the test sample at a given contamination level $\alpha$ is above a threshold contamination level and statistically significant, the contamination detection workflow 400 can call a contamination event.

In some embodiments, the population model is informed by a test sample call file (e.g., single variant call file 412), a population call file (e.g., MAF call file 414), and a set of variant call files (e.g., multiple variant call files 422). The test sample call file includes the observed variant allele frequencies $VAF_S$ for a single test sample. The variant allele frequency of the test sample $VAF_S$ can include observed variant allele frequencies VAF of any number of SNPs at any number of sites k. Similarly, the population call file includes the minor allele frequencies of a population of test samples ($MAF_P$). The minor allele frequency of the population of test samples $MAF_P$ can include the minor allele frequencies MAF of any number of SNPs of the population at any number of sites k. The set of variant call files includes the variant allele frequencies for a set of test samples ($VAF_B$). The set of variant allele frequencies for a set of test samples can include variant allele frequencies VAF of any number of SNPs at any number of sites k.

V.A Regression Model for MAF and Noise

In one embodiment, a contamination detection workflow 400 determines a likelihood that a sample is contaminated using observed sequencing data and a background noise model. In some examples, the observed sequencing data can be included in a test sample call file (such as single variant call file 412) and a population call file (such as MAF call file 414). The background noise model can be use a set of variant call files (such as multiple variant call files 422) to determine a background noise baseline. Here, for the purpose of example, the probability of contamination for a single SNP is based on the relationship between a test sample's variant allele frequency $VAF_S$, a population minor allele frequency $MAF_P$, and a background noise baseline generated from a set of variant allele frequencies $VAF_B$.

In one embodiment, the contamination detection workflow 400 uses a population model on a test sample including a number of SNPs. The population model can be represented as:

$$VAF_S = \alpha MAF_P + \beta N(VAF_B) + \epsilon \qquad (1)$$

where $\alpha$ is the contamination level, $\beta$ is the noise fraction for the test sample (i.e., number of noisy SNPs over number of non-noisy SNPs), N is the background noise model based on a set of variant allele frequencies $VAF_B$, and $\epsilon$ is a random error term determined by the regression.

In some cases, the variant allele frequency of the test sample $VAF_S$ and the minor allele frequency MAF of the population can include a negated variant allele frequency VAF and a negated minor allele frequency MAF. Negated variant allele frequencies and negated minor allele frequencies allow the data used by the population model to be similarly scaled such that data from homozygous alternate alleles and homozygous alleles in a test samples are similarly analyzed in the population model.

In one example embodiment, the population model includes each SNP i in a test sample. Each SNP i of the test sample is associated with a site k (i.e., genomic position) and any number of reads of the test sample can be associated with site k. Therefore, each SNP i of a test sample has a variant allele frequency VAF associated with its site k. Further, each SNP i at site k is associated with a minor allele frequency MAF for that site k. The minor allele frequency MAF for site k is the minor allele frequency MAF for reads from multiple samples at site k. For example, a first SNP $i_1$ of a test sample is associated with a first site $k_1$. The variant allele frequency VAF for the site $k_1$ is determined to be 0.03 from 1235 reads in the test sample associated with the first site $k_1$. The minor allele frequency MAF at the first site $k_1$ associated with the SNP $i_1$ is determined to be 0.01 from $1 \cdot 10^8$ SNPs in the population. A second SNP $i_2$ of a test sample is associated with a second site $k_2$. The variant allele frequency VAF for the site $k_2$ is determined to be 0.81 from 1792 reads in the test sample associated with the site $k_2$. The minor allele MAF frequency at site $k_2$ associated with the SNP $i_2$ at the site $k_2$ is determined to be 0.90 from $1 \cdot 10^9$ SNPs in the population.

Therefore, the variant allele frequency of the test sample $VAF_S$ can be represented as:

$$VAF_S = \Sigma_k \Sigma_i VAF_k^i \qquad (2)$$

where $VAF_S$ is the variant allele frequency of the test sample, the summation over k indicates that the variant allele frequency $VAF_S$ includes the variant allele frequency of SNPs at all sites k included in the test sample, and the summation over i indicates that the variant allele frequency VAF at site k includes all SNPs i at site k. Similarly, the minor allele frequency of the population $MAF_P$ can be represented as:

$$MAF_P = \Sigma_k \Sigma_i MAF_k^i \qquad (3)$$

where $MAF_P$ is the minor allele frequency of the population, the summation over k indicates that the minor allele frequency MAF includes the minor allele frequency MAF of SNPs of the population at all sites k included in the test sample, and the summation over i indicates that there is a minor allele frequency MAF associated with each SNP i at a site k of the test sample.

In one example embodiment, for a given test sample, there are three possible observed genotypes for each SNP i at a site k possible: homozygous reference 0/0, heterozygous 0/1, and homozygous alternative 1/1, where 0 represents the reference allele and 1 the alternative allele. In an uncontaminated test sample, the variant allele frequency values observed are expected to be close to 0, 0.5 and 1 for genotypes 0/0, 0/1 and 1/1, respectively. However, in a contaminated sample, the variant allele frequency values can be expected to shift from 0, 0.5, and 1, as the SNPs vary across the population, and thus, have a higher likelihood of being present in a contaminating sample. Modifying the variant allele frequencies VAF of the homozygous reference and homozygous alternative alleles such that the population model can analyze all genotypes of a test sample is beneficial.

Therefore, in some embodiments, the population model can, for some SNPs i, negate variant allele frequencies VAF for some SNPs such that the population model can more easily process the variant allele frequency VAF data. In one example embodiment, the variant allele frequency VAF for SNPs i at site k ($VAR_k^i$) included in the test sample can be described by:

$$VAF_k^i = \begin{cases} VAF_k & \text{if } 0 < VAF_k < 0.2 \\ NA & \text{if } 0.2 \le VAF_k \le 0.8 \\ 1 - VAF_k & \text{if } 0.8 < VAF_k < 1.0 \end{cases} \qquad (4)$$

where $VAR_k^i$ is the variant allele frequency VAF for an SNP i at site k of the test sample, $VAF_k$ is the variant allele frequency of all SNPs of the test sample at site k, and NA indicates that an SNP will not be considered. Here, the variant allele frequency VAF for SNP i at site k of the test sample ($VAF_k^i$) is the determined variant allele frequency for the SNPs at site k ($VAF_k$) if the SNP i is a homozygous reference genotype call. A homozygous reference call is a reference call with a variant allele frequency VAF of SNPs at site k greater than 0.0 and less than 0.2 ($0 < VAF_k < 0.2$). The variant allele frequency for an SNP i at site k of the test sample ($VAR_k^i$) is not considered (marked as "NA" above) if the SNP i is a heterozygous reference genotype call. A heterozygous reference call is a reference call with a variant allele frequency VAF of SNPs at site k greater or equal to than 0.2 and less than or equal to 0.8 ($0.2 \leq VAF_k \leq 0.8$). Finally, the variant allele VAF frequency for an SNP i at site k of the test sample ($VAF_k^i$) is 1 less the determined variant allele frequency $VAF_k$ for all the SNPs at site k if the SNP i is a homozygous alternative reference call. A homozygous alternative reference call is a reference call with a variant allele frequency VAF of SNPs at site k greater than 0.8 and less than 1.0 ($0.8 < VAF_k < 1.0$).

In some embodiments, the population model can, for some SNPs i, negate the minor allele frequencies MAF based on the variant allele frequency for an SNP i at site k such that the population model can more easily process the data. For example, the minor allele frequency for an SNP i at site k can be described by:

$$MAF_k^i = \begin{cases} MAF_k & \text{if } 0 < VAF_k < 0.2 \\ NA & \text{if } 0.2 \leq VAF_k \leq 0.8 \\ 1 - MAF_k & \text{if } 0.8 < VAF_k < 1.0 \end{cases} \quad (5)$$

where $MAF_k^i$ is the minor allele frequency MAF associated with SNP i at site k of the test sample, $MAF_k$ is the minor allele frequency of population SNPs at site k, NA indicates that an SNP will not be considered, and VAR is the variant allele frequency of the SNPs of the test sample at site k. Here, the minor allele frequency MAF associated with SNP i at site k of the test sample ($MAF_k^i$) is the minor allele frequency for the SNPs of the population at site k ($MAF_k$) if the SNP i is a homozygous reference genotype call. The minor allele frequency for an SNP i at site k of the test sample ($MAF_k^i$) is not considered (NA) if the SNP i is a heterozygous reference genotype call. Finally, the minor allele frequency associated with an SNP i at site k of the test sample ($MAF_k^i$) is the 1 less the determined minor allele frequency $MAF_k$ for all the SNPs at site k if the SNP i is a homozygous alternative reference call.

The population model can also include a background noise model N based on the variant allele frequencies from a set of variants ($VAF_B$). The background noise model N can be used to distinguish a background noise baseline that is generated during sequencing of each SNP, such as, for example, during processes 100 and 300. The introduced noise may be from the sequence context of a variant and, therefore, some sites k will have a higher noise level and some sites k will have a lower noise level. Generally, the noise model is the average variant allele frequency for healthy variants of the set of variants at a given site k. Therefore, a given SNP i at site k of the test sample can be associated with a background noise baseline associated with the site k. The background noise model N can determine a noise coefficient β representing the expected background noise baseline of each SNP.

In one approach, the population model regresses the contamination level α against the variant allele frequency for a test sample $VAF_S$, the minor allele frequency for the population $MAF_P$, and the background noise model N. That is, contamination detection workflow 400 calculates a contamination level α of a test sample using the associated variant allele frequency VAF, minor allele frequency MAF, and background noise model N for the SNPs of the test sample. Contamination detection workflow 400 determines a p-value of the contamination fraction a using the regression model across all SNPs of a test sample. Based on the p-value and the contamination level α, the contamination detection workflow 400 can determine that the test sample is contaminated. For example, in one embodiment, if the determined contamination level α is above a threshold contamination value (e.g., 3%) and the p-value is below a threshold p-value (e.g., 0.05) the sample can be called contaminated.

In an alternative approach, the population model can calculate two contamination levels using the variant allele frequencies VAF and minor allele frequencies MAF of the SNPs in the test sample. In one example, the population model can include a first regression including a first contamination level $\alpha_1$ using SNPs with homozygous alternative reference calls and a second regression including a second contamination level $\alpha_2$ using SNPs with homozygous reference calls. If a significant regression p-value is observed from both regressions, contamination detection workflow 400 can determine that the test sample is contaminated. In this case, using two regression equations to detect a contamination event provides stronger evidence for contamination than a single regression equation.

V.B Example Workflow for Detecting Contamination with MAF and Noise Model

Processing system 200 can be used to detect contamination in a test sample. For example, using the contamination detection workflow 400 a contamination event can be detected based on the relationship between the variant allele frequencies for a set of SNPs of a test sample and the associated minor allele frequencies and background noise baseline for each SNP of the test sample.

Figure 5:
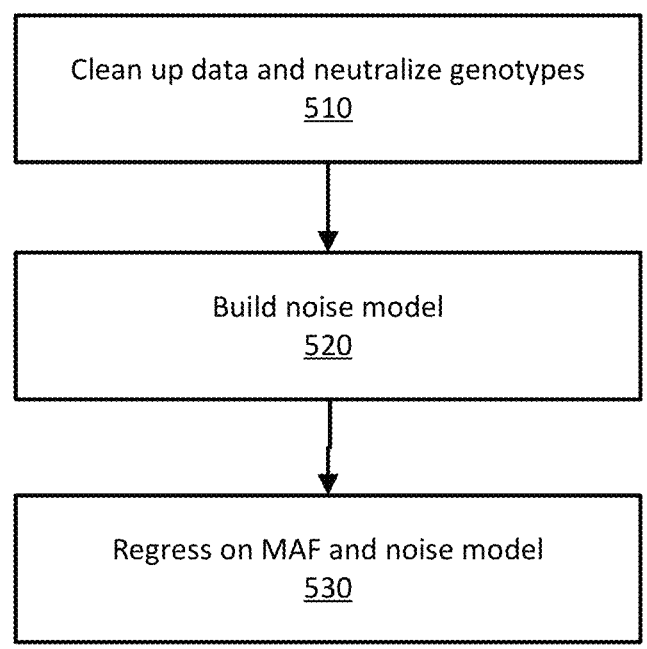
FIG. 5 illustrates a flow chart of a method for detecting contamination in a test sample using a population model, according to one example embodiment.

FIG. 5 illustrates a flow diagram demonstrating a contamination detection method 500 using a population model performed in accordance with workflow 400 of FIG. 4. The detection method 500 of this embodiment includes, but is not limited to, the following steps.

At step 510, the sequencing data obtained from a test sample (e.g., using the process 300) is cleaned up and genotypes are neutralized. For example, data cleaning may include filtering out non-informative SNPs, removing SNPs with no-calls, removing SNPs with a depth of less than, for example, 1000, removing any heterozygous SNPs (SNPs having variant allele frequencies from 0.2 to 0.8), and removing non-informative SNPs (SNPs having variant allele frequencies of 0.0 or 1.0). Homozygous alternative SNPs with variant allele frequencies VAF 0.8 to 1.0 are then negated (variant frequency 0.95 becomes 0.05) such that all variant allele frequency data can be linearly compared to minor allele frequency data of the population using the population model of contamination detection workflow 400. In some examples, the minor allele frequency MAF values are also negated based on a given test samples' genotype (similar to the variant allele frequency negation) before the regression is performed.

At step 520, a background noise model is built. For example, the background noise model generates a background noise baseline calculated from the minor allele frequency of the SNPs across healthy variant samples. The background noise model generates a noise coefficient which provides an estimate of the expected noise for each of the SNPs.

At a step 530, the variant allele frequencies VAF for a plurality (or set) of SNPs in a test sample is regressed against the population minor allele frequency MAF and the background noise model N to determine a contamination event.

In one example, the regression determines a p-value for a contamination level α. If the contamination level α is above a threshold and the p-value is below a threshold, a contamination event may be called.

V.C. Example Uncontaminated and Contaminated Samples

Contamination workflow 400 can determine a contamination event using a population model (i.e., method 500). That is, the population model analyzes variant allele frequencies of a number of SNPs at a number of sites k in a test sample and their associated minor allele frequencies and a background noise model. Generally, the population model analyzes the data based on the genomic position of the SNP in the test sample (e.g., site k as referred to above).

Figure 6A:
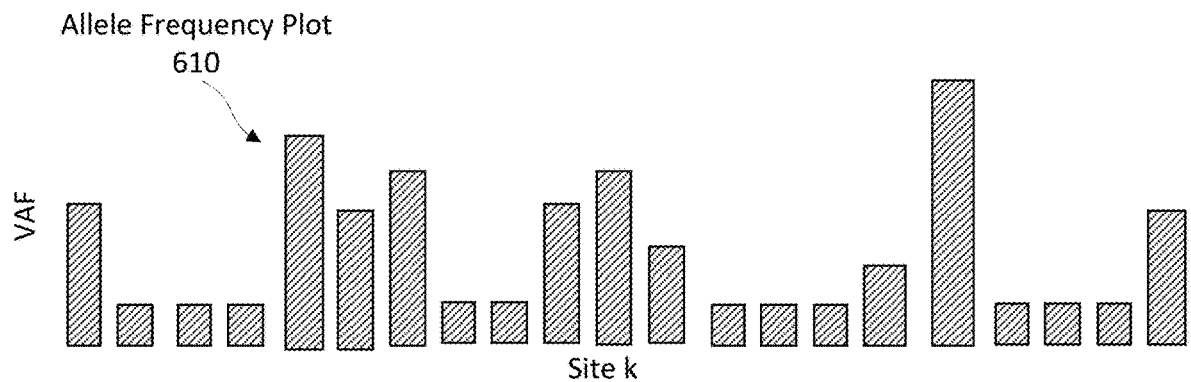
FIGS. 6A-6C are allele frequency plots for the variant allele frequency for a sample, minor allele frequency for a population, and background noise frequency for a set of test samples, according to one example embodiment.

FIG. 6A is an allele frequency plot 610 showing the variant allele frequency VAF for a number of homozygous SNPs from a test sample. Each bar in plot 610 represents a number of SNPs i at site k of the test sample and the height of the bar represents the variant allele frequency for all SNPs at site k.

Figure 6B:
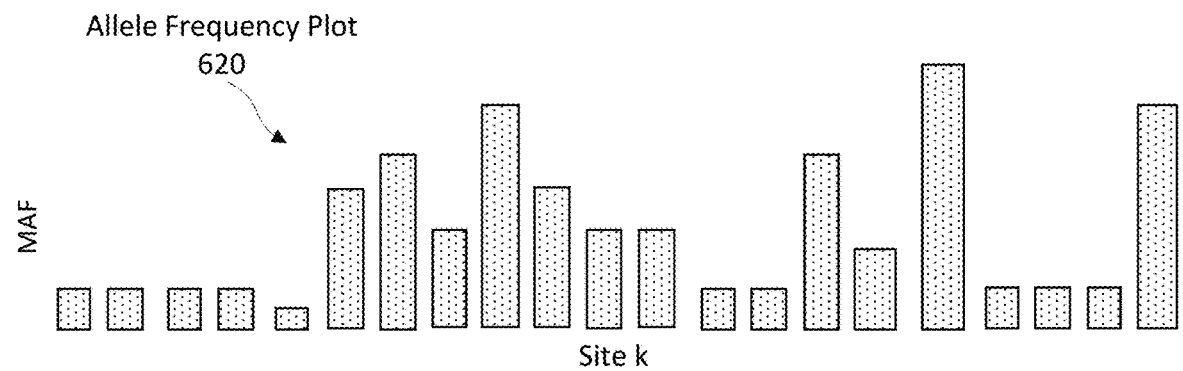

FIG. 6B is an allele frequency plot 620 showing the population minor allele frequency for a number of SNPs from a population. Each bar in plot 620 represents a number of SNPs i at site k from the population and the height of the bar represents the minor allele frequency for all SNPs at the site k.

Figure 6C:
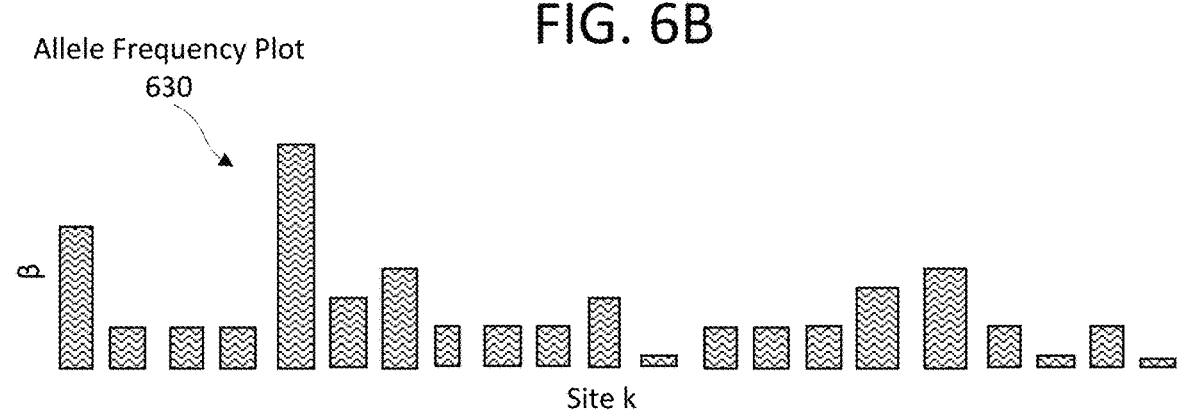

FIG. 6C is an allele frequency plot 630 showing a background noise model for the same SNP sites. Each bar in plot 620 represents a number of SNPs i at site k used to generate the background baseline from a set of healthy variants. The height of each bar in plot 630 represents the noise coefficient R for each site k. The noise coefficient is a representation of a "frequency" of noise for each SNP site k.

Figure 7A:
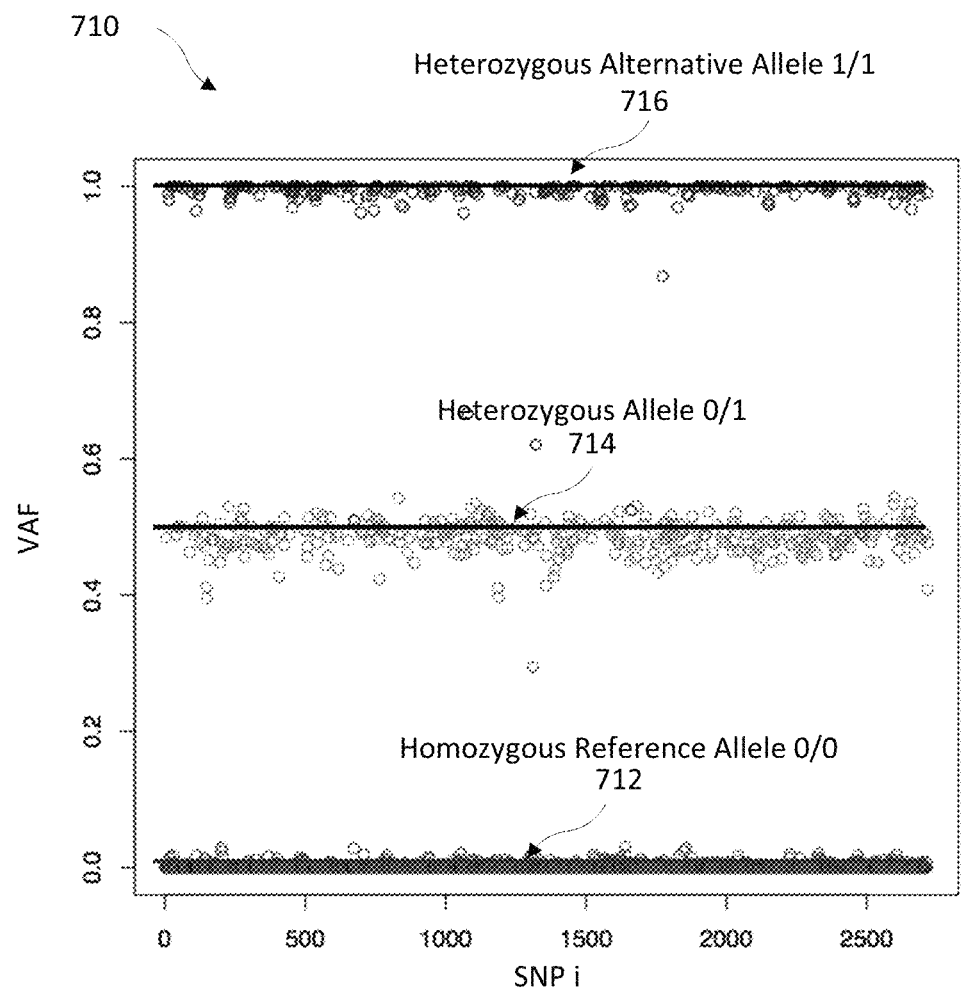
FIGS. 7A-7B are variant allele frequency distribution plots for a contaminated and uncontaminated sample, according to one example embodiment.

As previously described, the variant allele frequency for an SNP i at a given site k is based on the genotype of the SNP at that site k. FIG. 7A is a variant allele frequency distribution plot 710 (herein referred to as simply a "VAF distribution plot") showing the variant allele frequencies VAF for a set of SNPs in an uncontaminated sample. In plot 710, the x-axis represents each SNP i of a test sample, and the y-axis represents the variant allele frequency VAF of each SNP i at site k. As shown, the SNPs can be designated as homozygous reference alleles 0/0 712, heterozygous alleles 0/1 714, and homozygous alternative alleles 1/1 716. In this example, some noise is observed in the heterozygous allele region 714, i.e., the variant allele frequency VAF varies from 0.5. Variation in the VAF from 0.5 may be due to a higher sequencing coverage for one allele relative to the other allele. For the homozygous reference alleles (0/0) and the homozygous alternative alleles (1/1), divergence from variant allele frequencies VAF of 0 or 1, respectively, is much less, indicating a minimal amount of noise. As noted above, the background noise baseline can be captured in the background noise model N of baseline batch component 420.

Figure 7B:
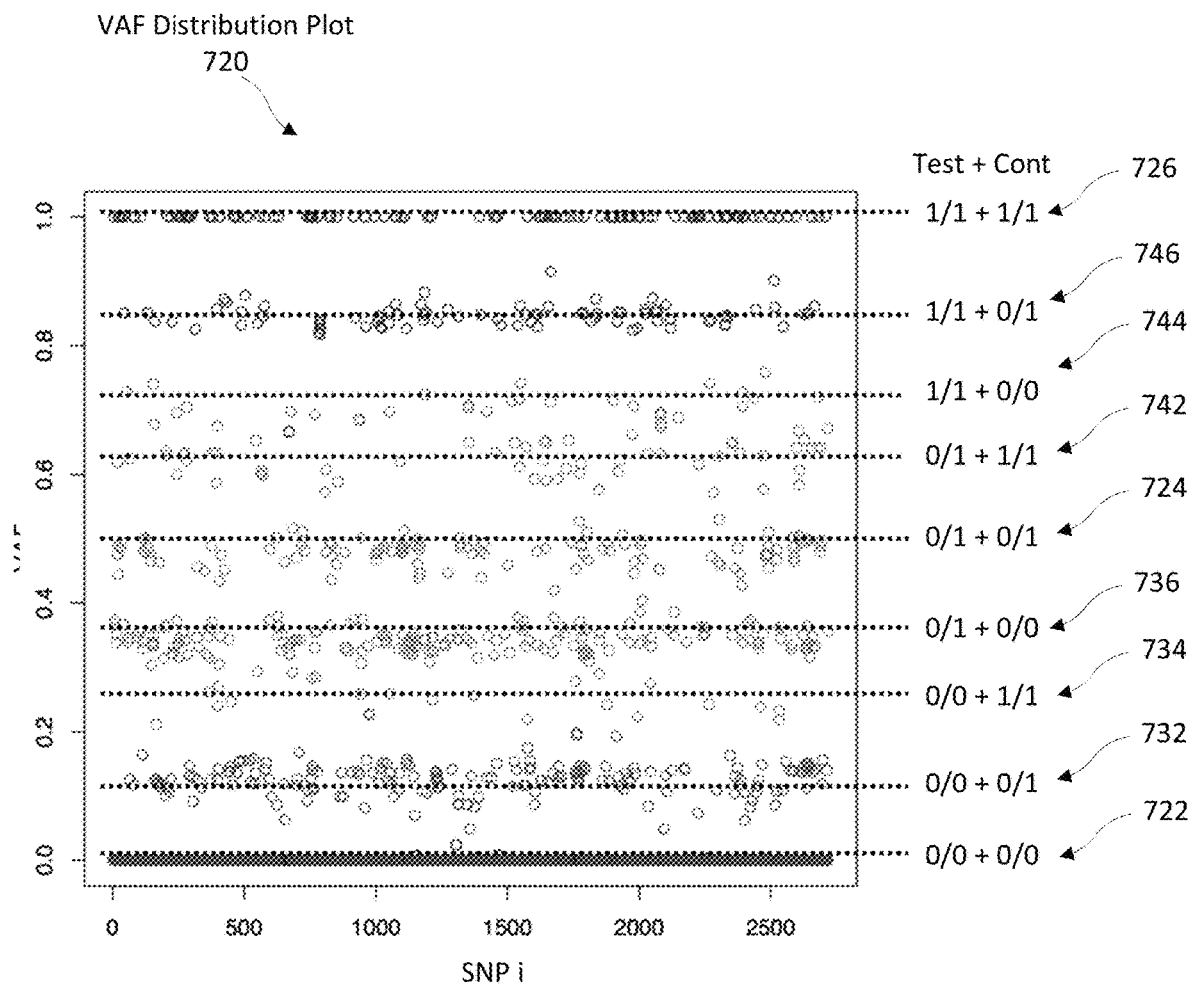

FIG. 7B is a VAF distribution plot 720 showing the variant allele frequencies VAF for a set of SNPs from a contaminated sample with a contamination level α 0.20 (or 20% contamination). In plot 710, the x-axis represents each SNP i of a test sample, and the y-axis represents the variant allele frequency VAF of each SNP i. As shown, nine distinguishable variant allele frequencies VAF are observed across the SNPs i of the test sample. As with uncontaminated sample of FIG. 7A, three expected bands are observed in the test sample for homozygous reference alleles (0/0) 722, heterozygous alleles (0/1) 724, and homozygous alternative alleles (1/1) 726. However, as the test sample (also referred to as a "source," more generally) in FIG. 4B is contaminated by a contaminating sample (also referred to as a "contaminant," more generally), six additional variant allele frequencies are observed. Here, the source and contaminant have different genotypes such that additional variant allele frequency VAF bands diverge from the three expected bands. As one example, a given SNP i at site k may be a homozygous reference allele (0/0) in the source and a heterozygous allele (0/1) in a contaminant for a test sample 732. Here, a variance of 0.15 in the variant allele frequency VAF of the homozygous reference allele 722 is due to the presence of the contaminant. Also illustrated are other allele combinations for the source and contaminant, including 0/0 source sample and 1/1 contaminant sample 734; 0/1 source sample and 0/0 contaminant sample 736; 0/1 source sample and 1/1 contaminant sample 742; 1/1 source sample and 0/0 contaminant sample 744; 1/1 source sample and 0/1 contaminant sample 746.

VAF distribution plots, such as the example plots 710 and 720 of FIG. 7A and FIG. 7B, respectively, can be generated as output of the contamination detection workflow 400 of FIG. 4 and provide a ready means to visualize a contamination event.

Figure 8A:
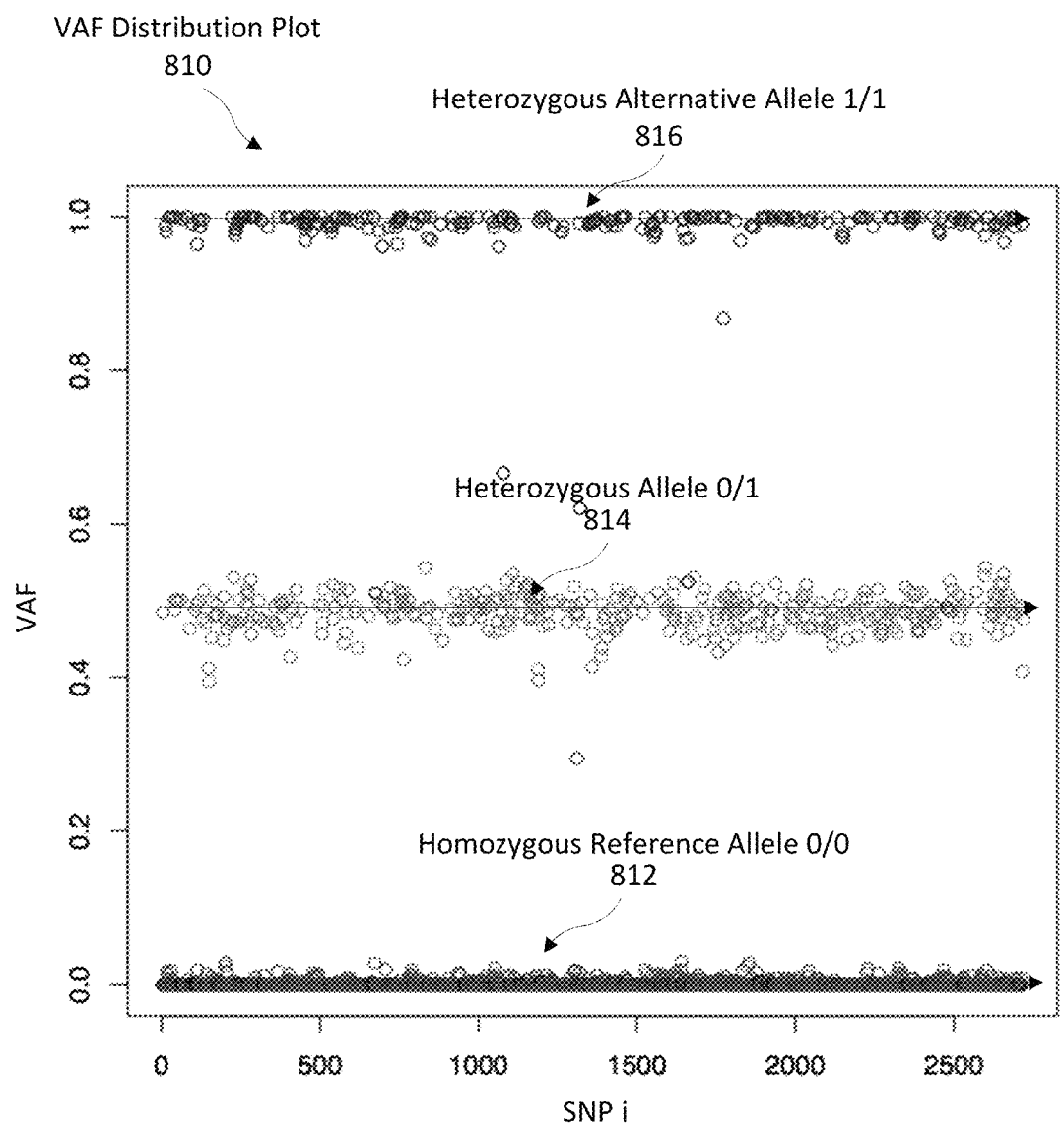
FIG. 8A is a variant allele distribution plot for a test sample with a contamination level of approximately 0.5%, according to one example embodiment.

FIG. 8 is a VAF distribution plot 810 showing the variant allele frequency VAF observed for a set of SNPs from a cfDNA test sample generated in silico with a contamination level α 0.5%. In plot 810, the x-axis represents each SNP i of a test sample, and the y-axis represents the variant allele frequency VAF of each SNP i of the test sample. FIG. 8A shows a plot 810 at 1× zoom. At 1× zoom, the three expected variant allele frequency bands are observed. That is, for example, homozygous reference alleles with a variant allele frequency of approximately 0.0 812, heterozygous alleles at a variant allele frequency VAF of approximately 0.5 814, and homozygous alternative alleles at variant allele frequency VAF of approximately 1.0 816. In this illustration, divergence from the variant frequencies of 0, 0.5, and/or 1 due to a contamination level α of 0.5% is minimal.

Figure 8B:
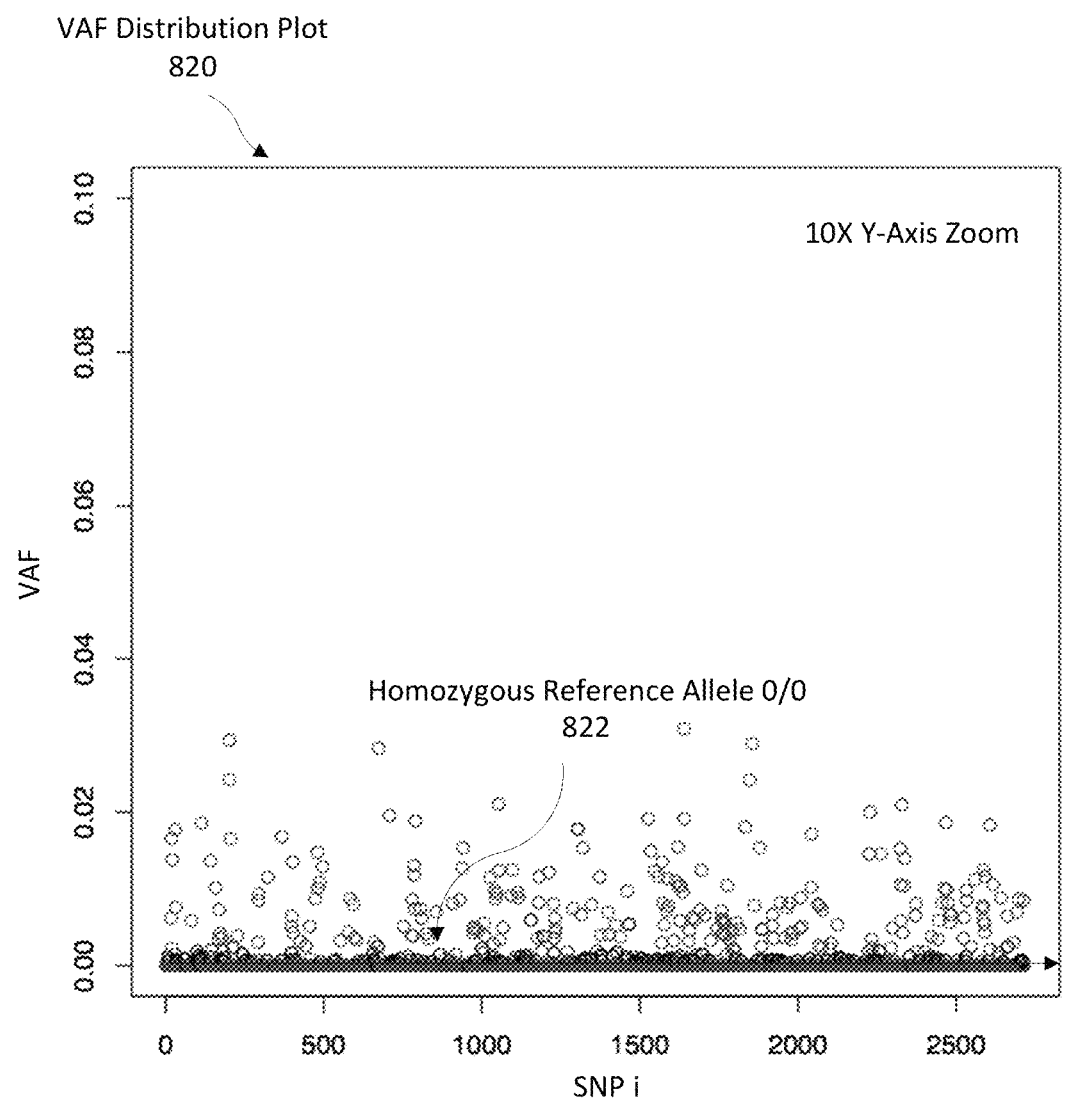
FIG. 8B is a variant allele distribution plot for the same test sample as FIG. 8A, but with a magnified y-axis, according to one example embodiment.

FIG. 8B is a VAF distribution plot 820 showing the variant allele frequency for the same set of SNPs from a cfDNA test sample of FIG. 8A (contamination level α 0.5%). In this plot, the y-axis magnification is increased tenfold and the y-axis centers around the homozygous reference alleles line 822. Here, the variant allele frequencies VAF for at least some of SNPs are diverging from 0.0. The divergence in the variant allele frequency VAF from 0.0 represents contamination and/or noise.

Figure 9A:
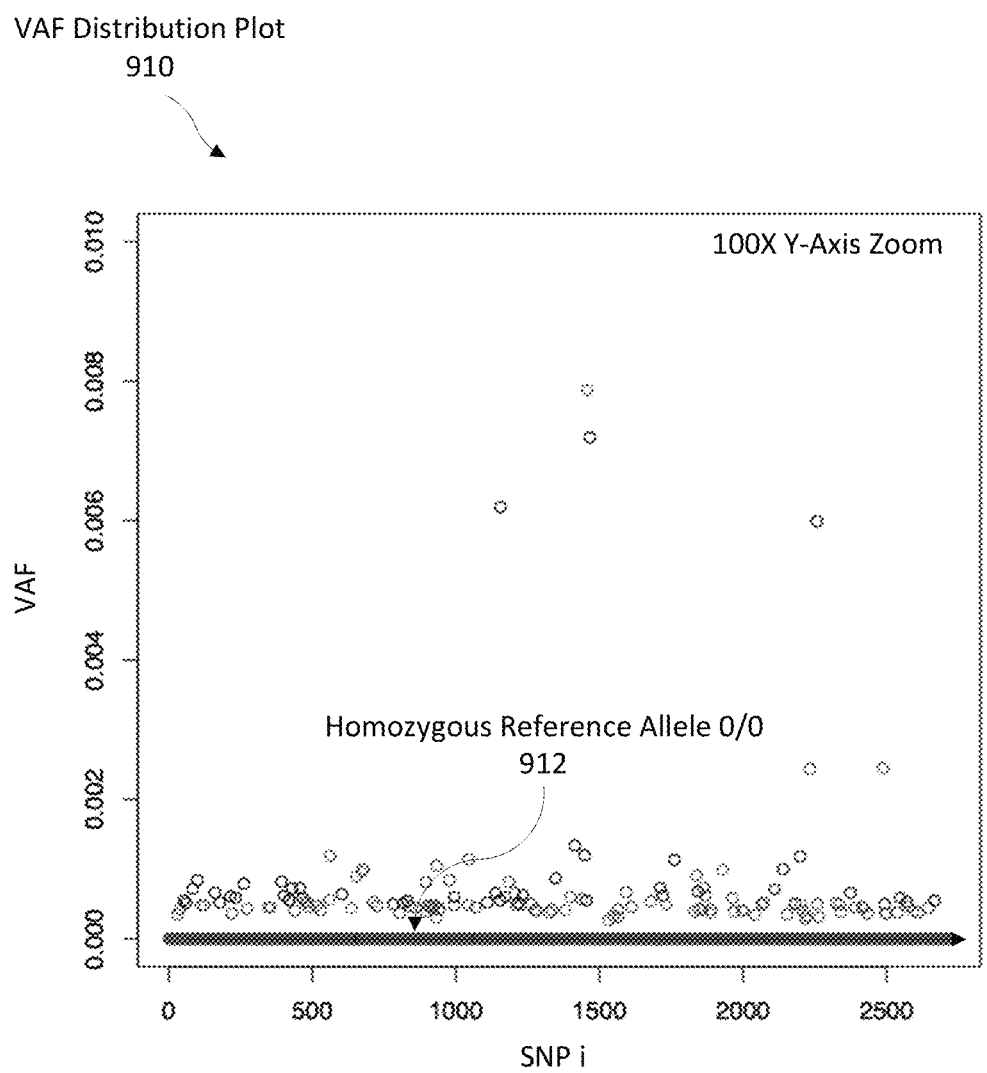
FIGS. 9A and 9B are variant allele distribution plots for an uncontaminated and contaminated test sample, respectively, with a magnified y-axis, according to one example embodiment.

Low levels of contamination can be more easily visually distinguished from background noise by comparing uncontaminated and contaminated samples at a 100× zoom level of the y-axis. FIG. 9A is a VAF distribution plot 910 showing the variant allele frequencies VAF for the homozygous reference alleles of a set of SNPs from an uncontaminated test sample (contamination level α≈0.0%). In plot 910, the x-axis represents each SNP i of a test sample, and the y-axis represents the variant allele frequency VAF of each SNP i of the test sample. In this plot, the y-axis magnification is increased one-hundredfold and the y-axis centers around the homozygous reference alleles line 912. Here, the variant allele frequencies VAF for at least some of SNPs are diverging from 0.0.

Figure 9B:
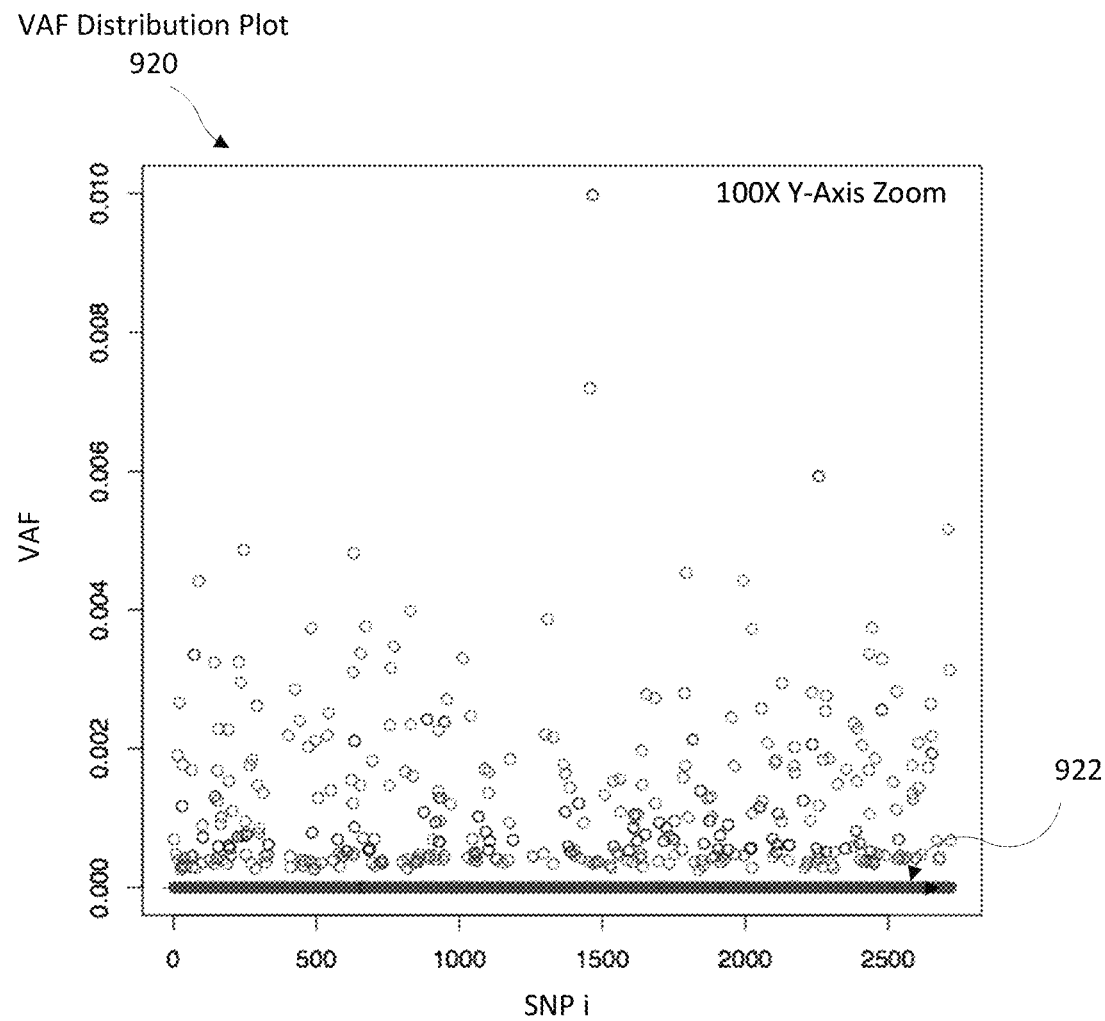

FIG. 9B is a VAF distribution plot 920 showing the variant frequencies for a set of SNPs for the homozygous reference alleles from a contaminated test sample with contamination level α 0.5% generated via in vitro titration.

In plot 920, the x-axis represents each SNP i of a test sample, and the y-axis represents the variant allele frequency VAF of each SNP i of the test sample. In this plot, the y-axis magnification is increased one-hundredfold and the axis centers around the homozygous reference alleles 922. Here, at contamination level α 0.5%, the number of SNPs diverging from 0.0 increases relative to an uncontaminated sample (for example, the sample of FIG. 9A).

Contamination detection workflow 400 using a population model, for example as described with respect to method 500 above, can be used to distinguish contamination from background noise in a contaminated test sample and detect a contamination event. In one embodiment, contamination detection workflow 400 can be trained (e.g., via training module 455) using a set of training samples (e.g., training datasets 456) to distinguish a contamination event from a background noise baseline. For example, the contaminated sample of FIG. 9B is an example of a contaminated sample generated via in vitro titration that can be used to train contamination detection workflow 400 and set a threshold for calling a contamination event versus a normal background noise baseline.

The previously described example population model runs a linear regression using a coefficient of linear regression that corresponds to the contamination level α. The contamination level α is selected as the coefficient of regression because SNPs that exist in high frequencies across the population (for example, a minor allele frequency MAF of about 50%) have a higher likelihood of being present in a contaminating sample. That is, the higher the minor allele frequency MAF of SNPs at a site k, the higher the likelihood that the SNPs will be present in the contaminating sample when not present in the test sample. Thus, when the variant allele frequencies VAF of SNPs at site k that may be related to a contaminating sample are regressed against population minor allele frequency MAF at the same site k, a coefficient of linear regression can be determined that correlates to the contamination level α.

Figures 10A, 10B:
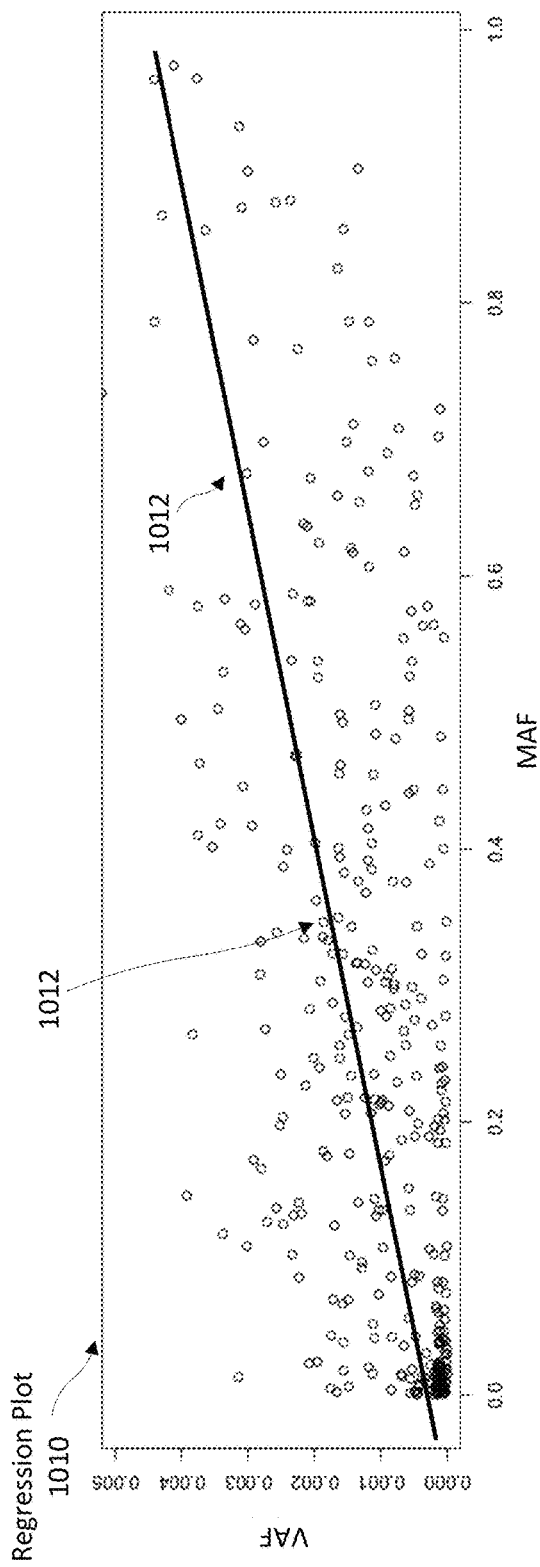
FIGS. 10A and 10B are regression plots illustrating the results of a linear regression for a contaminated an uncontaminated sample, respectively, according to one example embodiment.

For example, FIG. 10A shows a regression plot 1010 of the variant allele frequencies VAF (y-axis) against population minor allele frequency MAF (x-axis) for a plurality of SNPs in a test sample that is contaminated. Plot 1010 shows a regression line 1012 determined for the data set. In this example, the slope of the regression line is substantially positive indicating that the contamination level α is large. If the population model determines that the contamination level α has a low p-value, contamination detection workflow 400 may call a contamination event.

In another example, FIG. 10B shows a regression plot 1020 of the variant allele frequencies (y-axis) against population MAF (x-axis) for a plurality of SNPs in an uncontaminated test sample. Plot 1020 shows a regression line 1022 determined for the data set. In this example, the slope of the regression line is approximately zero indicating that the contamination level α is minimal. If the population model determines that the contamination level α has a low p-value, contamination detection workflow 400 may determine that there is not a contamination event.

V.D. Example Contamination Detection and Training

In some embodiments, contamination detection workflow 400 using a population model (e.g., method 500) can be trained using one or more known datasets. For example, a first dataset may include test samples with a known contamination level α, and a second dataset may include test samples known to be uncontaminated. Several different training datasets 456 can be used to train contamination detection workflow 400 using training module 455.

In various example embodiments, training datasets 456 may include: a copy number variation (CNV) baseline dataset from healthy individuals; an in vitro titration dataset; an in silico titration dataset; a cfDNA dataset from cancer patient samples; and a gDNA dataset from cancer patient samples. Table 1 shows an example summary of training datasets 456 that can be used to set the p-value threshold for a population model of contamination detection workflow 400. In this example, the training datasets included 244 uncontaminated samples and 50 contaminated samples with a contamination faction a between about 0.2% and about 20%. The CNV baseline dataset was used to test specificity. The in vitro (n=6 samples with a 0.4% contamination level and n=10 uncontaminated samples) and in silico titration (n=42 at contamination fractions ranging from 0.2% to 10%) datasets were used to test sensitivity. The cfDNA dataset was used to test contamination detection workflow 400 using a population model (e.g., method 500) using real cfDNA samples from cancer patients.

TABLE 1

Summary of training datasets 156

| Dataset | Number of samples | Positives | Negatives | CNV |
|---|---|---|---|---|
| CNV baseline | 36 | 1 | 35 | NA |
| In vitro titration | 16 | 6 | 10 | NA |
| In silico titration | 42 | 42 | 0 | NA |
| Late stage cfDNA | 100 | 1 | 99 | Present |
| Late stage gDNA | 100 | 0 | 100 | NA |

Figure 11:
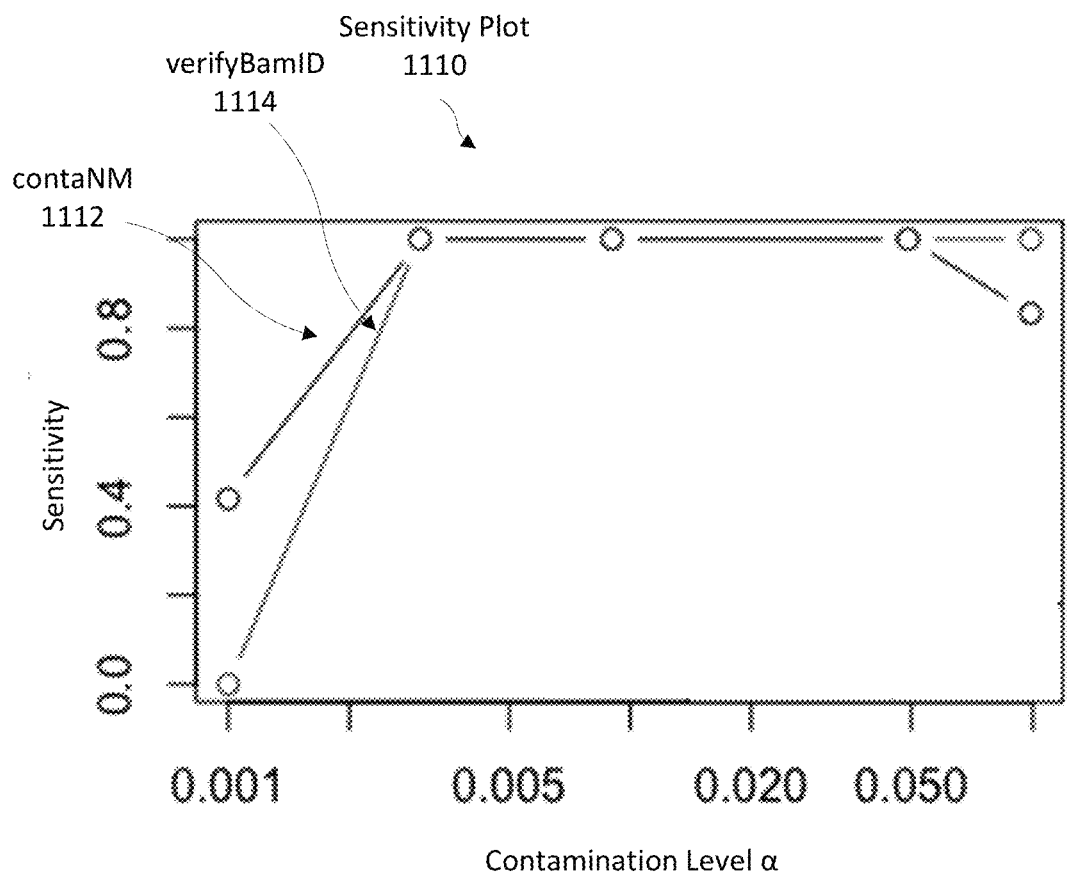
FIG. 11 is a sensitivity plot comparing the sensitivity of a contamination detection workflow to a commercially available product, according to one example embodiment.
Figure 12A:
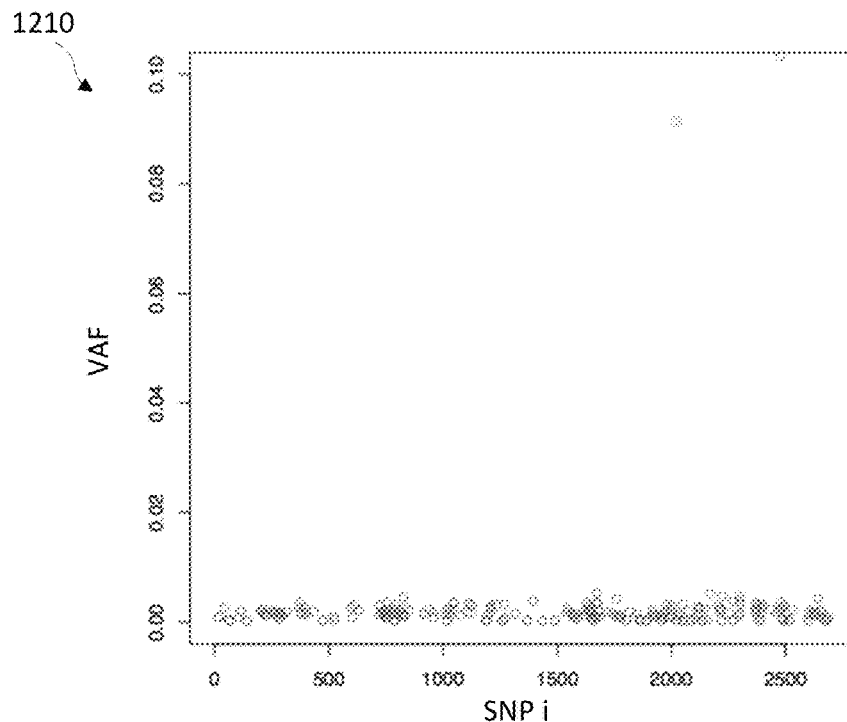
FIGS. 12A-12F are variant allele distribution plots for various test samples from late stage cancer patients, with one plot (FIG. 12F) showing a contamination event, according to one example embodiment.
Figure 12B:
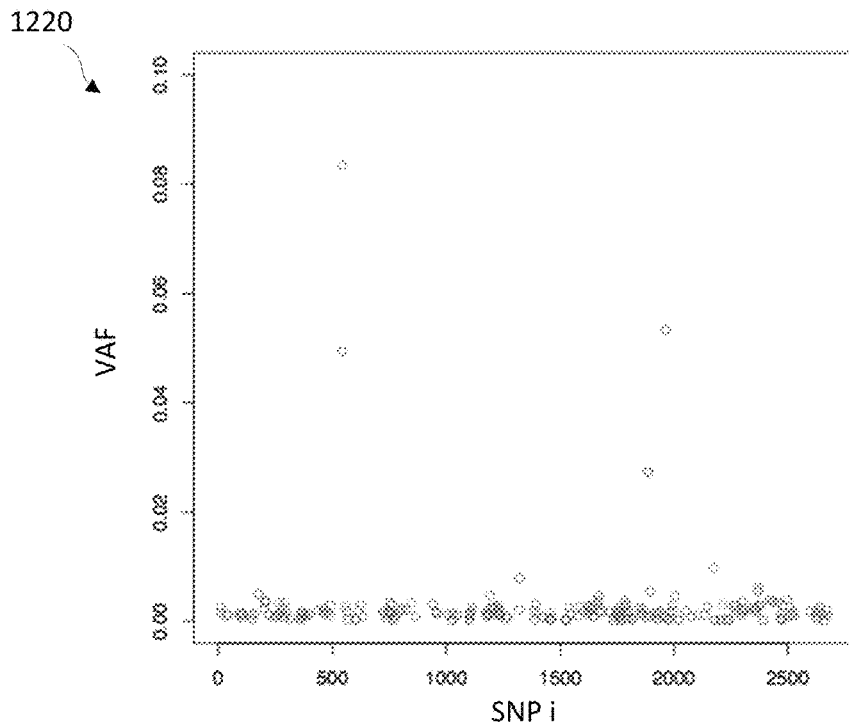
Figure 12C:
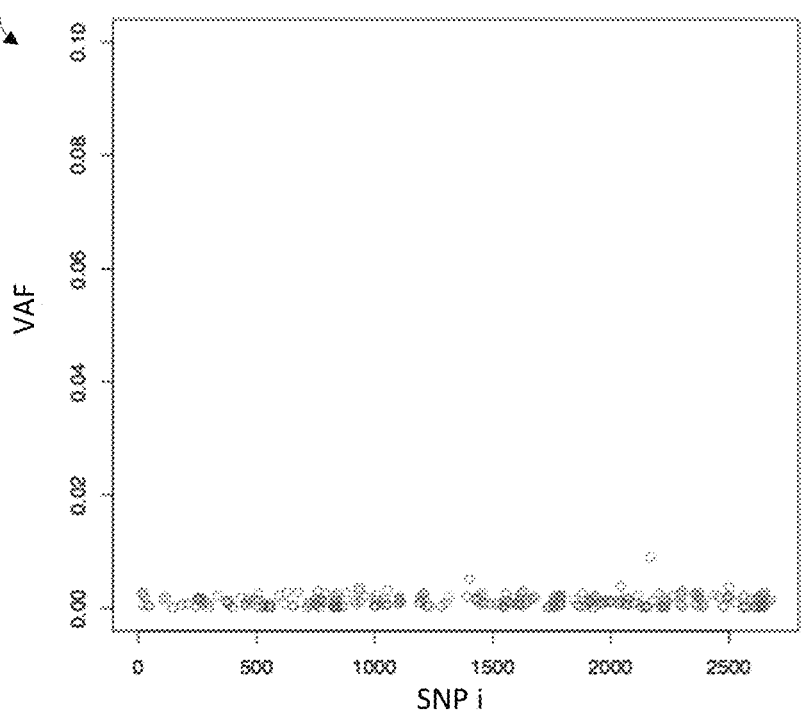
Figure 12D:
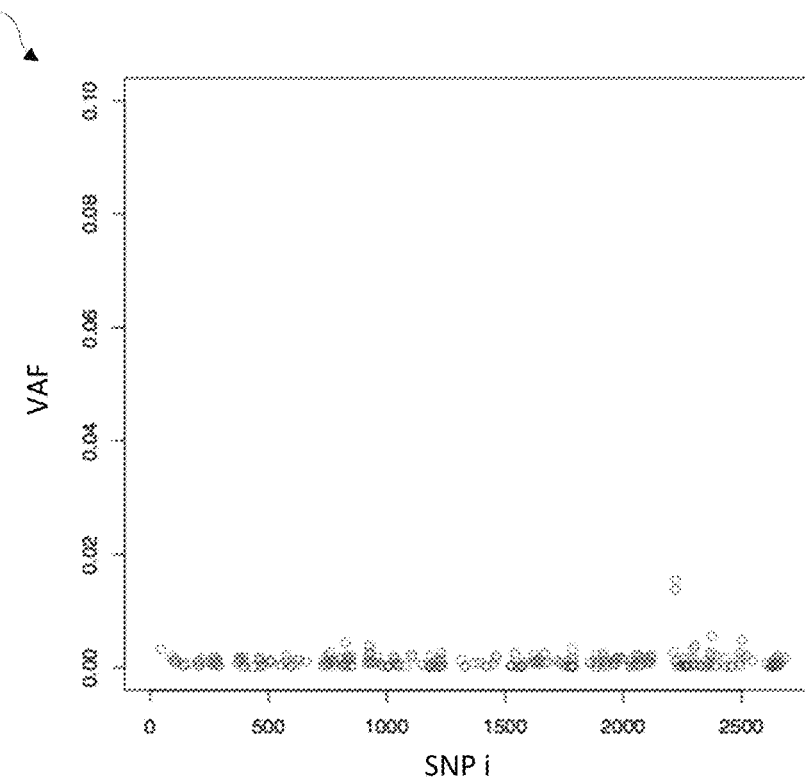
Figure 12E:
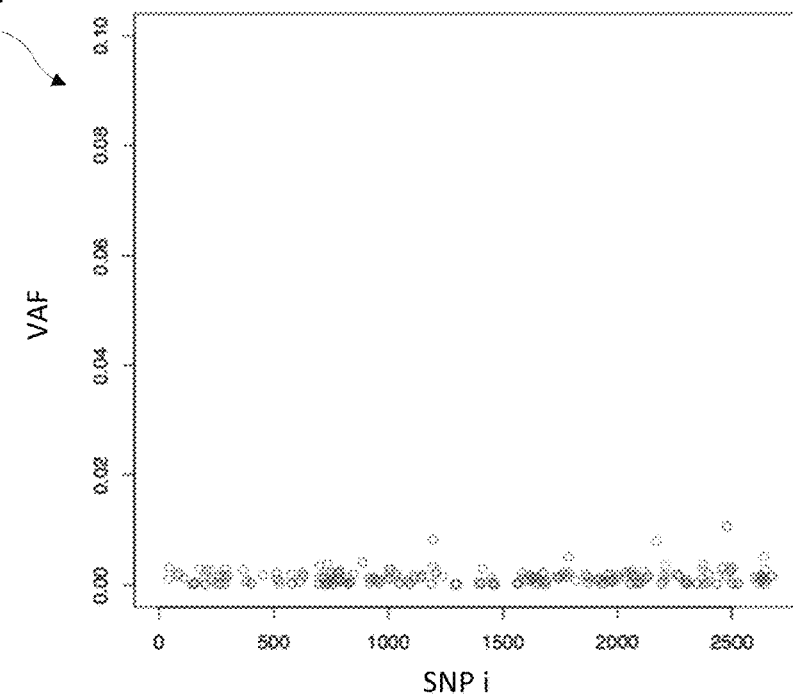
Figure 12F:
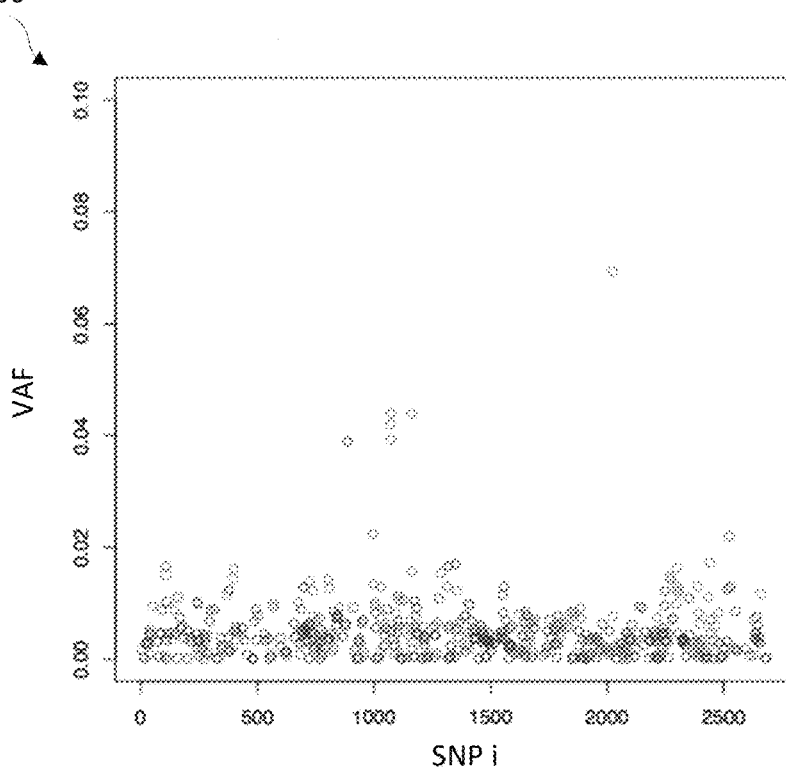

Sensitivity of contamination detection workflow 400 and/or contamination detection method 500 can be tested with individual samples generated in silico to create samples with contamination level α of, approximately, 0.2, 0.4, 1.5, and 10 percent. FIG. 11 is a sensitivity plot 1110 showing the in silico titration sensitivity of contamination detection workflow 400 using a population model (e.g., method 500). Contamination detection workflow 400 (herein referred to as "contaNM" 1112) was compared against a publicly available third-party software (herein referred to as "verifyBamID" 1114). verifyBamID verifies whether reads in a particular file match previously known genotypes for an individual (or group of individuals) and checks whether the reads are contaminated as a mix of the two samples. In the example of sensitivity plot 1110, contaNM determines contamination slightly better than verifyBamID, but both methods performed well for contamination levels a ranging from, approximately, 0.4% to 10%. Additionally, in this example, both verifyBamID and contaNM have a lower sensitivity at a contamination level α≈0.2% (contamination level α of 0.2% was undetected). Above contamination level α≈10%, the sensitivity of contamination detection using contaNM decreases. The decrease in sensitivity at higher levels of contamination level α is, for example, due to the exclusion of heterozygous genotypes by the population model used in contaNM. A separate algorithm designed to detect higher levels of contamination in a test sample (e.g., contamination level α≈20% or higher) can be included in contamination workflow 400.

FIGS. 12A-12F shows a series of VAF distribution plots (i.e., 1210 through 1260) giving the variant allele frequencies VAF for the homozygous reference alleles in cfDNA samples from 6 late stage cancer patients. Here, the SNPs are sorted along the x-axis in chromosome order (genomic order) and the variant allele frequency is on the y-axis. A contamination event is detected using contamination workflow 400 for test samples illustrated in plot 1260 of FIG. 12F. Stated differently, in this example a statistically significant determined contamination level α was detected in the sample corresponding to FIG. 12F. FIGS. 12A-12E illustrate test samples that are uncontaminated and thus where contamination detection workflow 400 does not determine/detect a contamination event.

FIGS. 13A-13F shows a series of VAF distribution plots (plots 1310 through 1360) giving the variant allele frequencies VAF for the homozygous reference alleles in cfDNA samples from 6 late stage cancer patients. Here, the SNPs are sorted along the x-axis in chromosome order (genomic order) and the variant allele frequency is on the y-axis. A contamination event is detected using contamination workflow 400 for test samples illustrated in plot 1350 of FIG. 13E and plot 1360 of FIG. 13F. FIGS. 13A-13D include test samples that are uncontaminated and contamination detection workflow 400 does not determine a contamination event.

Figure 13A:
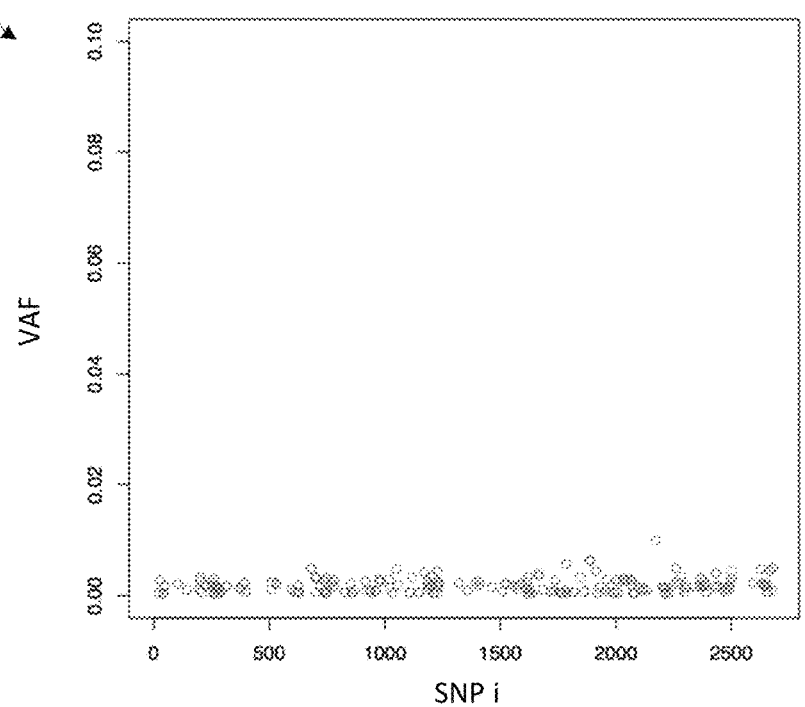
FIGS. 13A-13F are variant allele distribution plots for various test samples from late stage cancer patients, with two plots (FIGS. 13E-13F) showing a contamination event, according to one example embodiment.
Figure 13B:
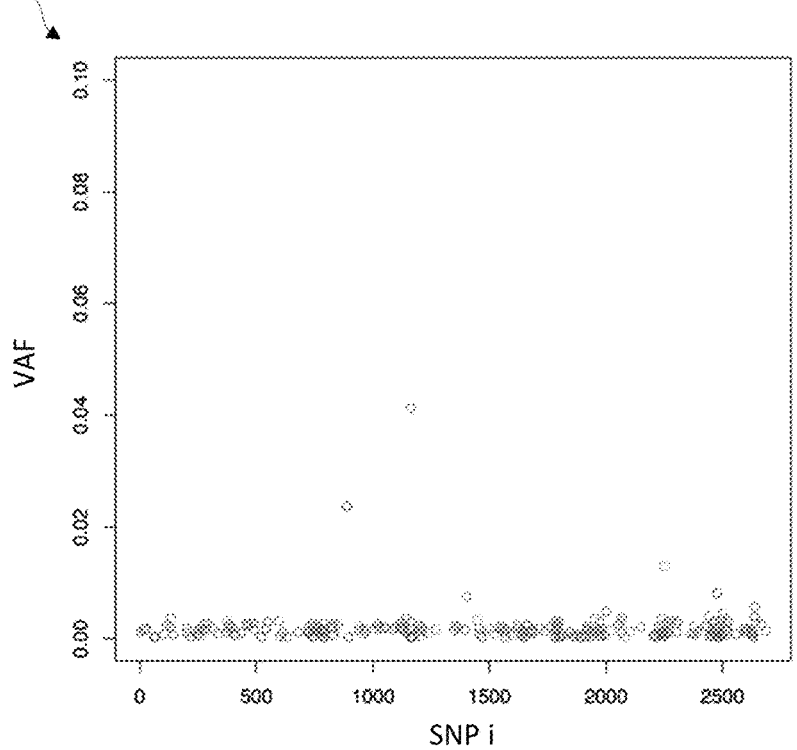
Figure 13C:
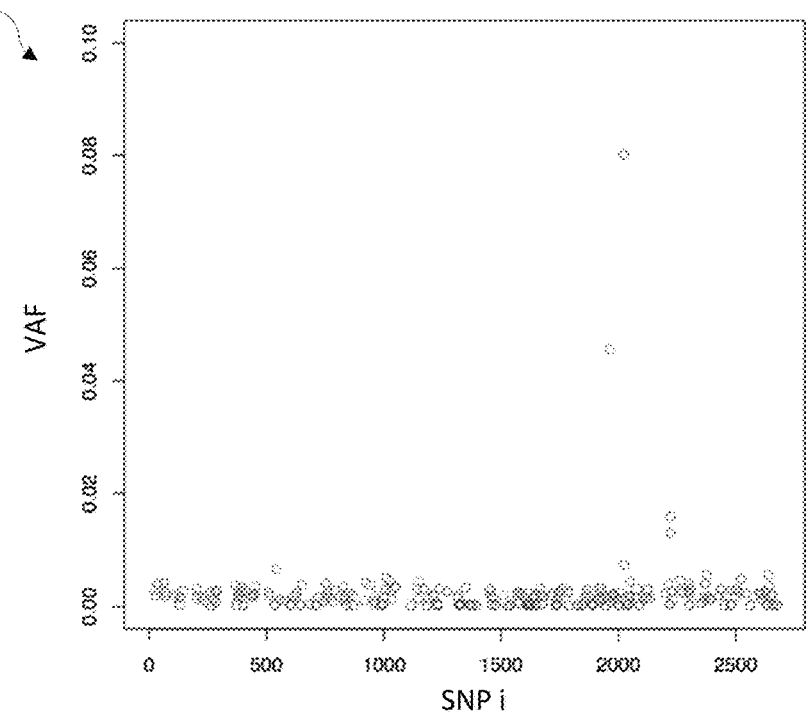
Figure 13D:
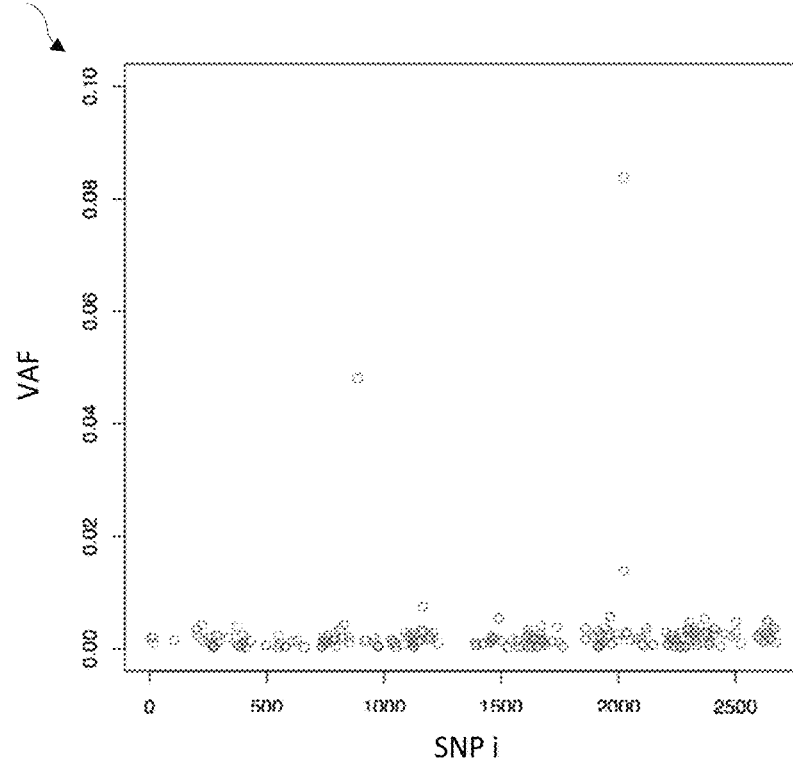
Figure 13E:
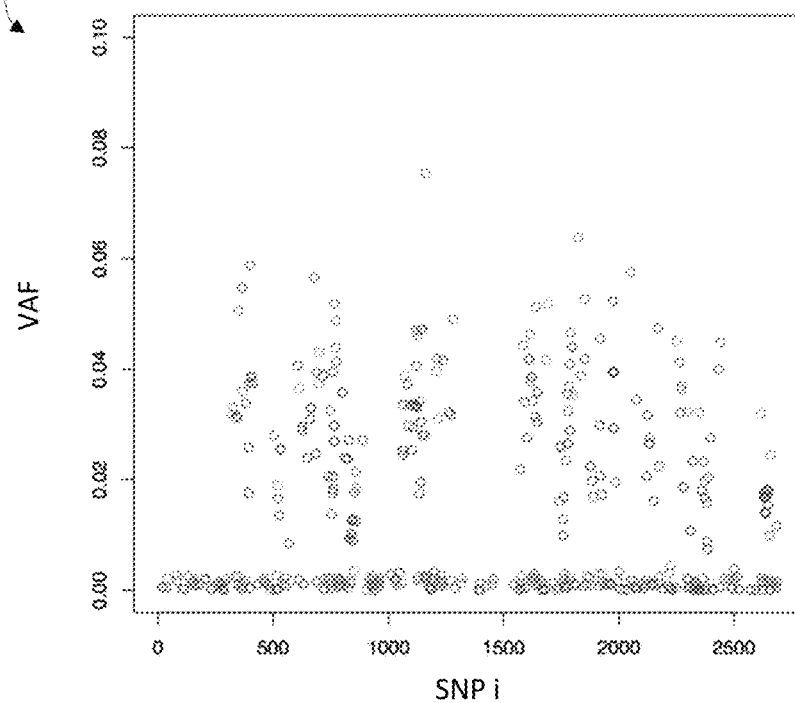
Figure 13F:
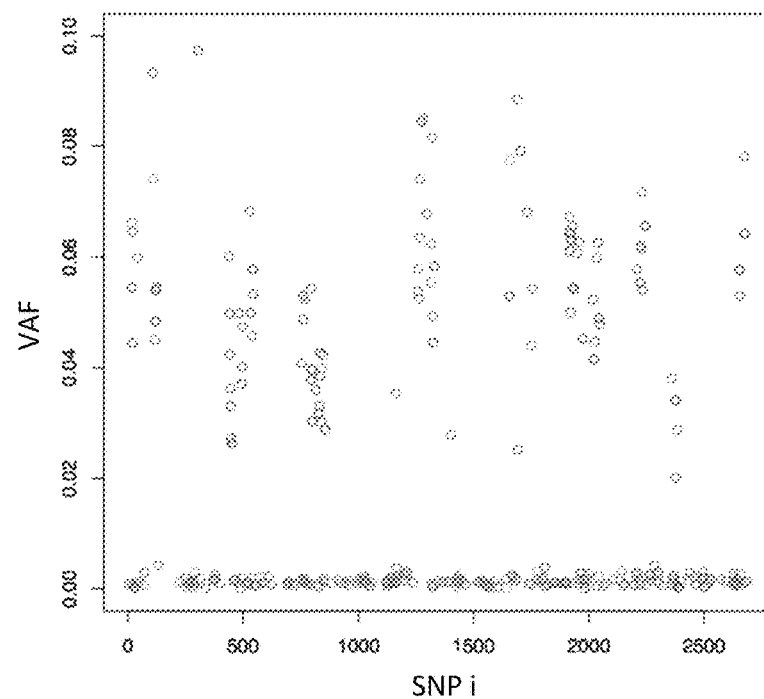
Figure 14A:
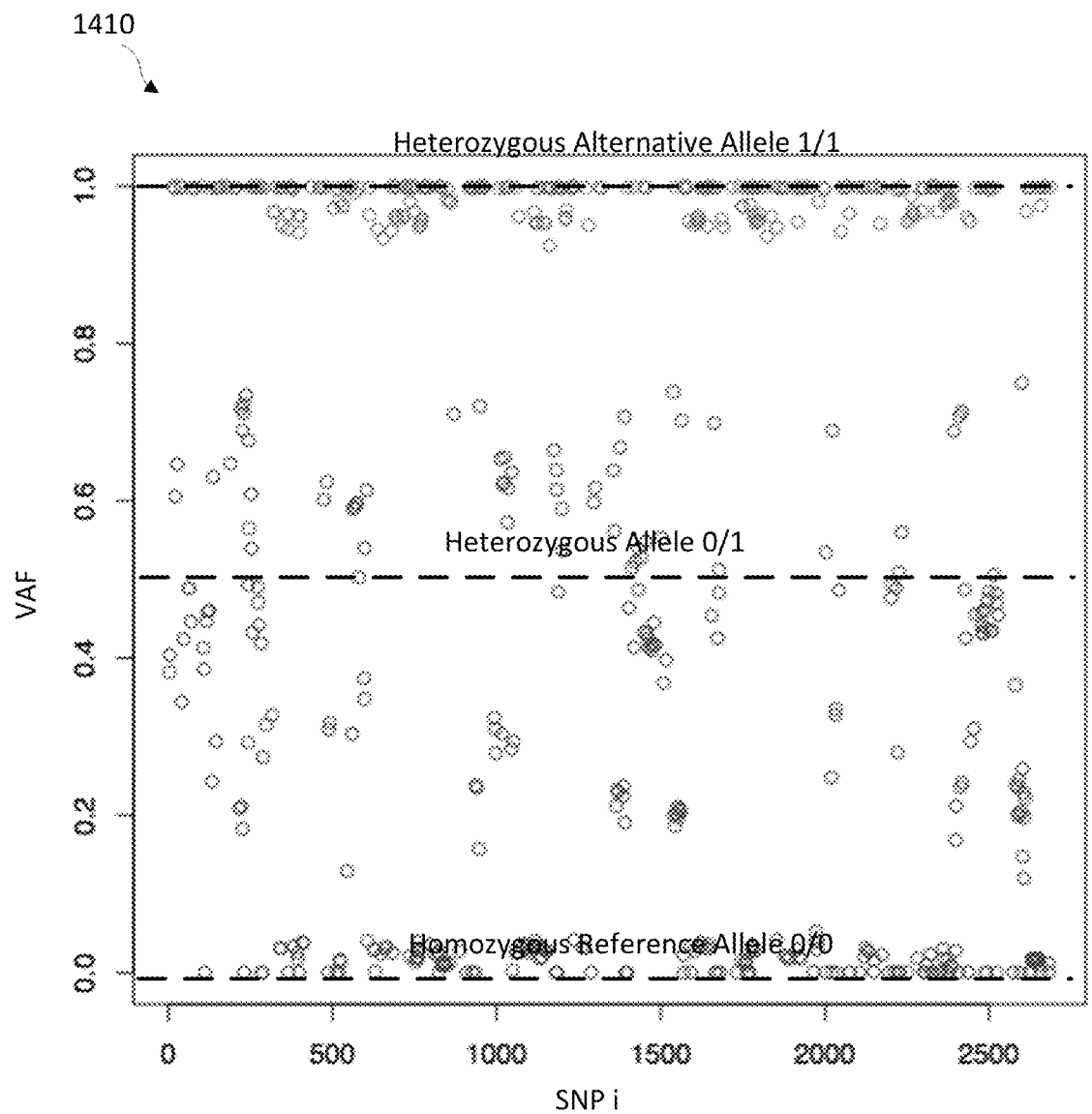
FIGS. 14A-14B are variant allele distribution plots for test samples including copy number variations, according to one example embodiment.
Figure 14B:
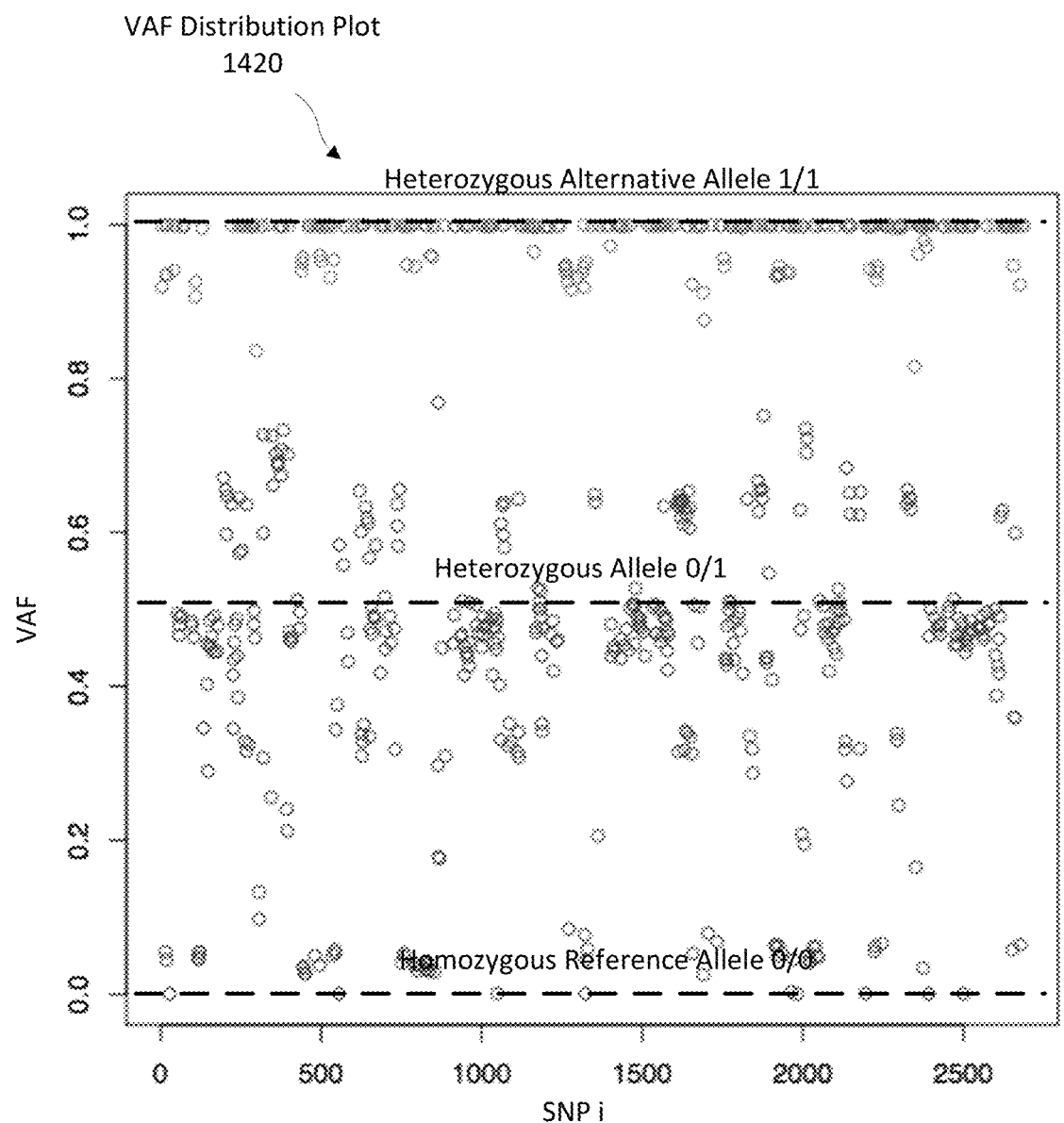

FIGS. 14A and 14B show VAF distribution plots 1410 and 1420, respectively, illustrating that the variant allele frequencies for a plurality of SNPs from the cfDNA samples from FIGS. 13E and 13F (rather than just those localized around VAF 0.0), respectively. Here, the SNPs are sorted along the x-axis in chromosome order (genomic order) and the variant allele frequency is on the y-axis. In this example, the variant allele frequencies VAF shown in VAF distribution plots 1410 and 1420 are different from the expected pattern for an uncontaminated test sample (e.g., plot 710 of FIG. 7A). The expected homozygous reference allele 0/0, heterozygous allele 0/1, and heterozygous alternative allele lines are shown for reference. The samples from plots 1350 and 1360 of FIGS. 13E and 13F were analyzed using the copy number variation caller 245 and were shown to include multiple copy number variations. Table 2 shows the CNV calls (using CNV caller for the cfDNA of the test sample illustrated in plot 1350 and Table 3 shows the CNV calls for the cfDNA of the test sample illustrated in plot 1360.

TABLE 2

CNV calls for test sample of FIG. 13E/14A

| Gene | chromosome | Targeted regions | Fold change | t-stat | q score/Pass |
|---|---|---|---|---|---|
| MYC | chr8 | 41 | 2.482 | 1074.158 | 22.422PASS |
| NBN | chr8 | 47 | 4.126 | NA | 50.672PASS |

TABLE 3

CNV calls for test sample of FIG. 13F/14B

| Gene | chromosome | Targeted regions | Fold change | t-stat | q score/Pass |
|---|---|---|---|---|---|
| MDM4 | chr1 | 33 | 1.843 | 276.202 | 11.083PASS |
| RICTOR | chr5 | 57 | 1.79 | 273.256 | 11.021PASS |
| E2F3 | chr6 | 48 | 2.999 | 2439.516 | 34.562PASS |
| MYC | chr8 | 41 | 2.399 | 1103.38 | 22.736PASS |
| NBN | chr8 | 47 | 2.486 | 1342.07 | 25.185PASS |
| FOXA1 | chr14 | 47 | 1.769 | 393.575 | 13.323PASS |

Referring again to plot 1410 of FIG. 14A and plot 1420 of FIG. 14B, heterozygous SNPs in some of the larger CNV regions appear in the homozygous SNP regions. The presence of these CNVs can result in contamination detection workflow determining a contamination event. This type of contamination event is generally not an issue for contamination detection workflow 400 unless the heterozygous SNP ratios at CNV regions are about less than 20% or more than about 80%. In contrast, CNVs are problematic for contamination detection using verifyBamID as described below with reference to FIG. 15.

Three modes of contamination detection workflow 400 using a population model are tested for specificity and sensitivity in detecting contamination: a contamination detection workflow 400 without a background noise model (herein referred to as "conta"), a contamination detection workflow 400 with a background noise model (corresponding to contamination detection method 500, herein referred to as "conta NM"), and a contamination detection workflow 400 with a background noise model that subtracts the determined background noise baseline (herein referred to as "conta NMS").

Figure 15:
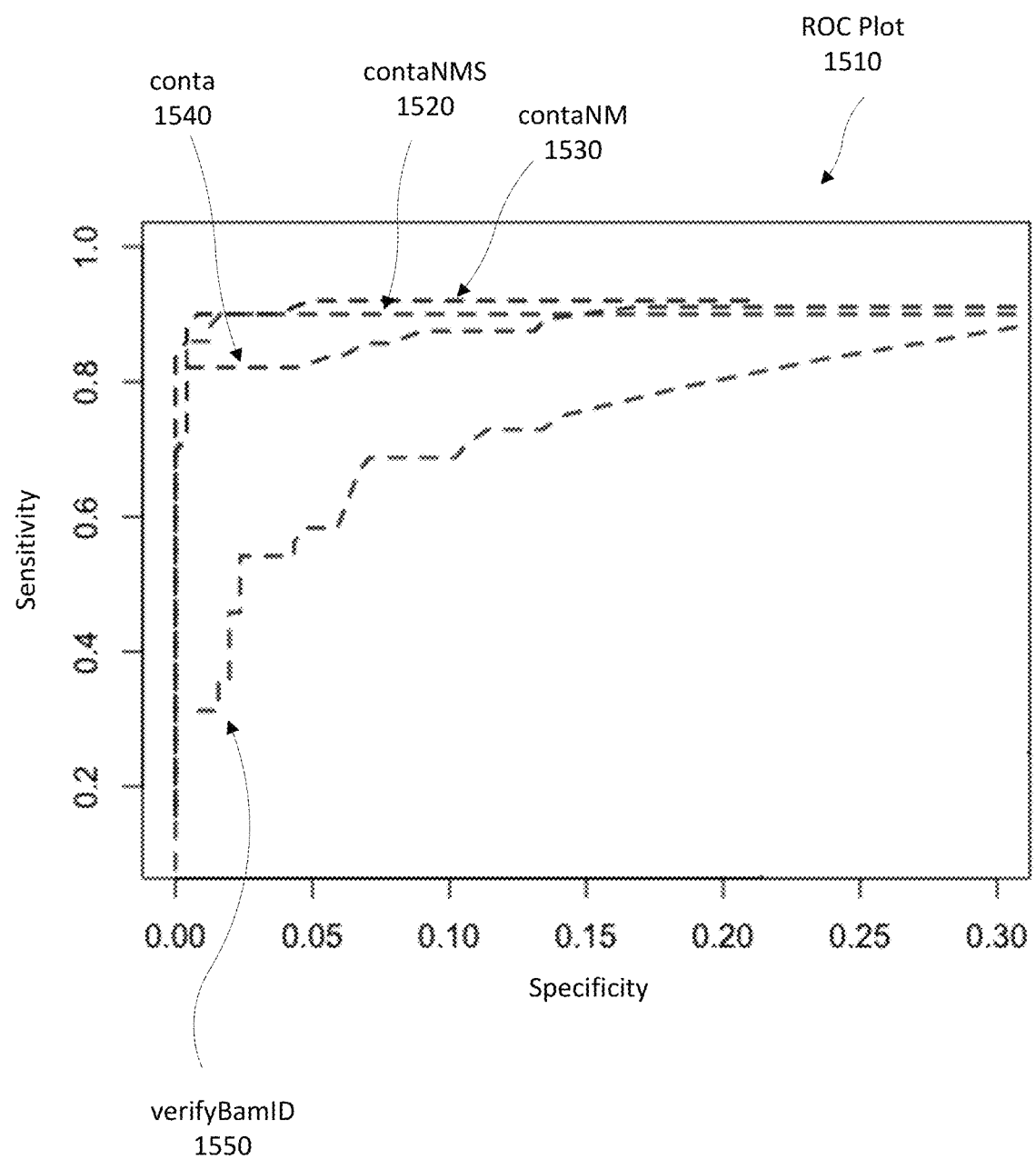
FIG. 15 is a ROC plot for a contamination detection workflow using three different population models, according to one example embodiment.

FIG. 15 is a ROC plot 1510 showing the receiver operating characteristic (ROC) curves for contamination level α thresholds for the three contamination detection workflows 400 and the third party tool verifyBamID. Sensitivity and specificity were testing using the datasets shown in Table 1. Plot 1510 shows a ROC curve 1520 for the contaNMS workflow, a ROC curve 1530 for the contaNM workflow (method 500), a ROC curve 1540 for the conta workflow, and a ROC curve 1550 for verifyBamID. As shown in FIG. 5, contaNM (ROC curve 1530) performed the best for contamination detection. In this example, contaNM has a contamination threshold that maximized sensitivity and specificity is p-value <1e-26 (sensitivity=70%, specificity=99.2%).

Further, as shown in FIG. 15, verifyBamID 1550 performed relatively poorly compared to the three modes of contamination detection workflow 400. This observation is in contrast to the performance of verifyBamID described with reference to FIG. 11, where the dataset used was the in silico titration dataset. In this example, the late stage cfDNA dataset that includes CNVs was included in the ROC analysis. The use of a dataset that includes CNVs demonstrates that the verifyBamID algorithm is susceptible to calling a false positive (determining a contamination event when a sample is uncontaminated) when CNVs are present in the test sample. For verifyBamID, the threshold was set as likelihood differential −4000. None of the processes tested achieved 100% sensitivity. In one example, this can be because of a portion of the titration including a contamination fraction of α≈0.2% are undetected using any threshold (e.g., about 60% missed calls).

The performance of contamination detection workflow 400 including a noise background model (method 500 contaNM) was assessed using four additional test datasets. Table 4 below shows a summary of the test datasets that were used in contaNM. In total, the test datasets included 22 positive contaminated samples, 314 negative samples and a contamination range of about 0.2 to about 50%. The in silico titration #2 dataset has a contamination fraction a of 0.4%. The early stage cfDNA dataset has a contamination rate of about 5%.

TABLE 4

Summary of test datasets

| Dataset | Number of samples | Positives | Negatives | CNV |
|---|---|---|---|---|
| In silico titration #2 | 13 | 13 | 0 | NA |
| Late stage cfDNA | 55 | 0 | 55 | Present |
| Late stage gDNA | 55 | 0 | 55 | NA |
| Healthy normal samples | 35 | 0 | 35 | NA |
| Early stage cfDNA | 178 | 9 | 169 | NA |

Figure 16:
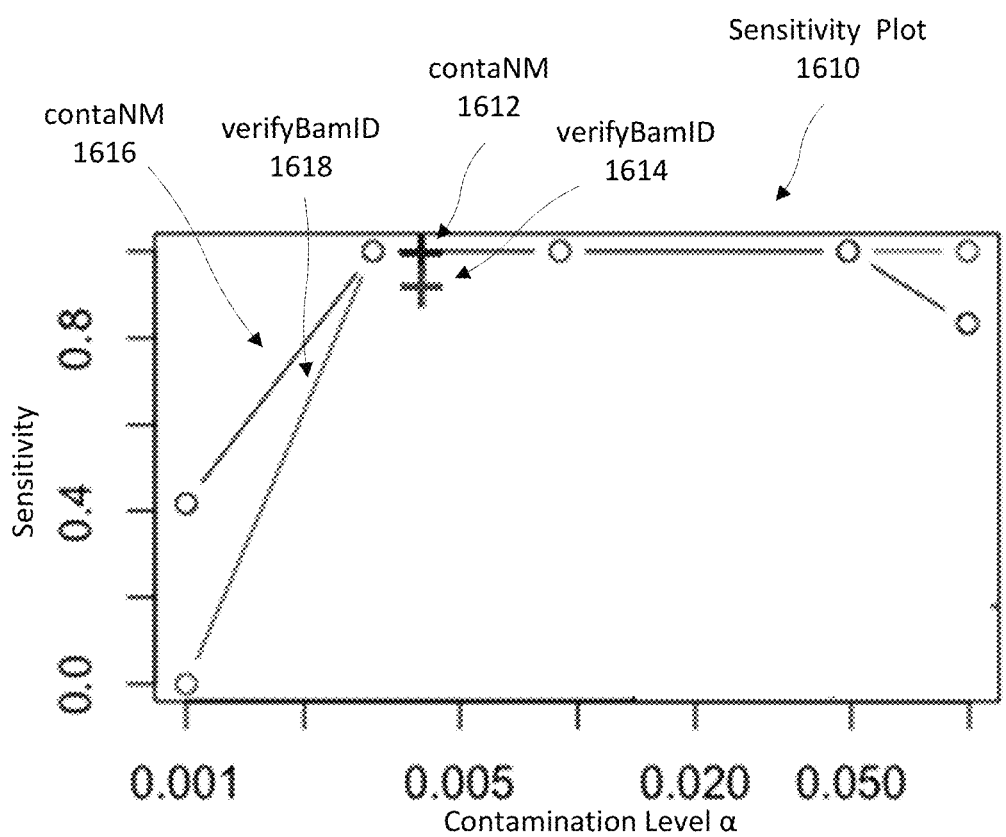
FIG. 16 is a sensitivity plot comparing the sensitivity of a contamination detection workflow using different data sets.

FIG. 16 is a sensitivity plot 1610 showing a sensitivity test for contamination detection workflow 400 (contaNM) and the third party tool verifyBamID using the in silico titration #2 dataset of Table 4. The plus signs (+) indicate the performance of contamination detection workflow contaNM (+1612) and verifyBamID (+1614) for the in silico titration test samples with a contamination level α 0.4% using the data of Table 4. The lines indicate the performance of contamination detection workflow 400 using the training datasets of Table 1 (line 1616 for contaNM, and line 1618 for verifyBamID).

Table 5 shows a summary of the performance of contamination detection workflow 400 (conta NM) using the test sample datasets shown in Table 4 and the test plus training sample datasets. In this example, test datasets shown in Table 4 plus training datasets shown in Table 1). For the test sample datasets (n=336), 18 positive calls were made, including 16 true positive calls and 2 false positive calls for a positive predictive value of 89%; 318 negative calls were made, including 312 true negatives calls and 6 false negative calls for a specificity of 99.3%. For the false negative calls, 2 calls were for samples with a contamination fraction of about 50%. In total, the datasets included 22 positive samples, including 16 true positives and 6 false negatives and the sensitivity of contamination detection was 81%.

For the test plus training samples (n=660 samples), 59 positive calls were made, including 55 true positive calls and 4 false positive calls for a positive predictive value of 93%; 601 negative calls were made, including 578 true negatives calls and 23 false negative calls for a specificity of 99.3%. In total there were 78 positive samples, including 55 true positives and 23 false negatives. For the test+training samples, most of the false negatives were due to missed positive calls for the 0.2% synthetic titration samples. Specificity was 99.3% with a confidence interval CI of [98.66%, 99.94%]. The positive predictive value was 93%. For verifyBamID, the overall test specificity (including cfDNA) was 79.05% with a confidence interval of [72.49%, 85.61%].

TABLE 5

Contamination algorithm specificity on test datasets

| Metric | Test Samples | Test + Training Samples |
|---|---|---|
| n | 336 | 660 |
| True positives | 16 | 55 |
| False positives | 2 | 4 |
| True negatives | 312 | 578 |
| False negatives | 6 | 23 |
| Sensitivity | 81% | 71%* |
| Positive predictive value | 89% | 93% |
| Specificity | 99.3% | 99.3% |
|  |  | CI = [98.66%, 99.94%]** |

Referring again to FIG. 4, plots 610, 620, 630, 710, 720, 810, 820, 910, 920, 1010, 1020, 1110, 1210, 1220, 1230, 1240, 1250, 1260, 1310, 1320, 1330, 1340, 1350, 1360, 1410, 1420, as well as Tables 1 through 5 are examples of information that can be displayed via GUI 150 of contamination detection workflow 400.

VI. Detecting Contamination Using Contamination Probability and Noise

In another example embodiment of contamination detection workflow 400, the model for detecting contamination is a linear regression model based on a contamination probability generated from population minor allele frequencies, herein referred to as a "probability model" for convenience of description and delineation from the "population model" discussed previously. The probability model determines contamination by calculating a probability that the observed variant allele frequency for a test sample is statistically significant relative to a contamination probability and background noise baseline. That is, the probability model calculates a probability of observing a variant allele frequency VAF of a test sample at a given contamination level alpha of the probable contamination frequency generated from the population. If the population model determines that the observed VAF for the test sample at a given contamination level α is above a threshold contamination level and statistically significant, the detection workflow 400 can determine a contamination event.

In some embodiments, the probability model is informed by a test sample call file (e.g., single variant call file 412), a population call file (e.g., MAF call file 414), and a set of variant call files (e.g., multiple variant call files 422). The test sample call file includes the observed variant allele frequencies $VAF_S$ for a single test sample. The variant allele frequency of the test sample $VAF_S$ can include observed variant allele frequencies VAF of any number of SNPs at any number of sites k. Similarly, the population call file includes the minor allele frequencies MAF of a population of test samples. The minor allele frequency of the population of test samples MAF can include the minor allele frequencies of any number of SNPs of the population at any number of sites k. The set of variant call files includes the variant allele frequencies for a set of test samples, i.e. $VAF_B$. The set of variant allele frequencies for a set of test samples can includes variant allele frequencies at a number of SNPs at any number of sites k.

VI.A Regression Model for Contamination Probability and Noise

In one embodiment, a contamination detection workflow 400 determines a likelihood that a sample is contaminated using observed sequencing data and a background noise model. In some examples, the observed sequencing data can be included in a test sample call file (such as single variant call file 412) and a population call file (such as MAF call file 414). The background noise model can be use from a set of variant call files (such as multiple variant call files 422) to determine a background noise baseline. Here, for the purpose of example, the probability of contamination for a single SNP is based on the relationship between a test sample's variant allele frequency $VAF_S$, a contamination probability C based on a population minor allele frequency $MAF_P$, and a background noise baseline generated from a set of variant allele frequencies $VAF_B$.

In one embodiment, the contamination detection workflow 400 uses a population model on a test sample including a number of SNPs. The population model can be represented as:

$$VAF_S = \alpha C(MAF_P) + \beta N(VAF_B) + \in \quad (6)$$

where C is contamination probability based on the minor allele frequency of the population $MAF_P$, $\alpha$ is the contamination level for the population, $\beta$ is the noise fraction for the test sample, N is the background noise model generating a background noise baseline from the variant allele frequencies for a set of variants $VAF_B$, and $\varepsilon$ is a random error term determined by the regression.

Here, the variant allele frequency of the test sample $VAF_S$ and the minor allele frequency of the population $MAF_P$ are similarly defined as in Eqns. 2 and 3. That is, each SNP i of the test sample is associated with a site k and the variant allele frequency for an SNP i is the variant allele frequency based on all SNPs at site k in the test sample. Further, each SNP i of the test sample is associated with a minor allele frequency MAF of all SNPs of the population at site k.

In some embodiments, contamination detection workflow 400 uses a probability model based on the population minor allele frequency $MAF_P$. Therefore, the contamination probability associated with each SNP i at site k of the test sample can be represented as:

$$C(MAF_k{}^i) = C_k{}^i = \Sigma_k \Sigma_i C_k{}^i \quad (7)$$

where $C_k{}^i$ is the contamination probability associated with each SNP i at site k of the test sample, the summation over k indicates that the contamination probability C includes the minor allele frequency MAF of SNPs of the population at all sites k included in the test sample, and the summation over i indicates that there is a contamination probability C associated with each SNP i of the test sample.

The contamination probability represents the likelihood a sample is contaminated based on the minor allele frequency MAF and genotype of the SNP i at site k. In one example embodiment, contamination probability C for an SNP i at site k (CO) included in the test sample can be described as:

$$C_k^i = \begin{cases} 1 - (1 - MAF_k)^2 & \text{if } 0 < VF_k < 0.2 \\ NA & \text{if } 0.2 \leq VF_k \leq 0.8 \\ 1 - (MAF_k)^2 & \text{if } 0.8 < VF_k < 1.0 \end{cases} \quad (8)$$

where $C_k{}^i$ is the probability of contamination probability C associated with SNP i at site k of the test sample, $MAR_k$ is the minor allele frequency of population SNPs at site k, NA indicates that an SNP will not be considered, and $VAR_k$ is the variant allele frequency of the SNPs of the test sample at site k. Here, the contamination probability C associated with SNP i at site k of the test sample ($C_k{}^i$) is one less the quantity one less the minor allele frequency for SNPs of the population at site k squared $(1-(1-MAF_k)^2)$ if the SNP i is a homozygous reference genotype call. The contamination probability for an SNP i at site k of the test sample ($C_k{}^i$) is not considered (marked as "NA" above) if the SNP i is a heterozygous reference genotype call. Finally, the contamination probability C associated with SNP i at site k of the test sample ($C_k{}^i$) is one less the quantity one less the minor allele frequency for SNPs of the population at site k squared (i.e., $1-(1-MAF_k)^2$) if the SNP i is a homozygous reference genotype call.

In some embodiments, the probability model can include a background noise model N similar to the noise model described for detection workflow 400. That is, the noise model is the average variant allele frequency for healthy variants of the set of variants at a given site k (i.e., $VAF_B$). Therefore, a given SNP i at site k of the test sample can be associated with a background noise baseline associated with the site k. The background noise model N can determine a noise coefficient $\beta$ representing the expected background noise baseline of each SNP.

In this example, the probability model regresses the contamination level $\alpha$ against the variant allele frequency for a test sample $VAF_S$, the contamination probability C and the background noise model N. That is, contamination detection workflow 400 calculates a contamination level $\alpha$ of a test sample using the associated variant allele frequency VAF, contamination probability C, and background noise model N for the SNPs of the test sample. Contamination detection workflow 400 determines a p-value of the contamination fraction a of the SNPs in a test sample using the probability model. Based on the p-value and the contamination level $\alpha$, the contamination detection workflow 400 can determine that the test sample is contaminated. For example, in one embodiment, if the determined contamination fraction a is above a threshold contamination value (such as, for example, 3%) and the p-value is below a threshold p-value (such as, for example, 0.05) the sample can be called contaminated.

VI.B Example Workflow for Detecting Contamination with Contamination Probability and Noise Processing system 200 can be used to detect contamination in a test sample. For example, using the contamination detection workflow 400 a contamination event can be detected based on the relationship between the variant allele frequencies for a set of SNPs of a test sample and a contamination probability and background noise baseline for each SNP of the test sample.

Figure 17:
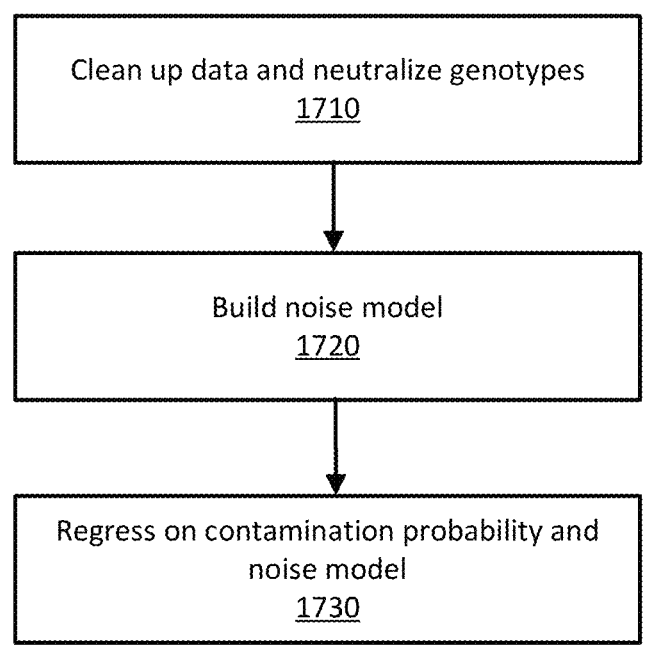
FIG. 17 illustrates a flow chart of a method for detecting contamination in a test sample using a probability model, according to one example embodiment.

FIG. 17 illustrates a flow diagram demonstrating a contamination detection method 1700 performed in accordance with workflow 400 of FIG. 4. The detection method of this embodiment includes, but is not limited to, the following steps.

At step 1710, the sequencing data is cleaned up and genotypes are neutralized similarly to step 510 of FIG. 5. The contamination probabilities for each SNP i at site k are determined based on the minor allele frequencies of the population at site k.

At step 1720, a background noise model is built. For example, the background noise model generates a background noise baseline calculated from the minor allele frequency of the SNPs across healthy samples. The background noise model generates a noise coefficient, which provides an estimate of the expected noise for each of the SNPs.

At a step 1730, the observed variant allele frequencies for a plurality (or set) of SNPs is regressed against the contamination probability of SNPs (based on MAF) and the background noise model to detect a contamination event.

VI.C Example Contamination Detection and Contamination Probability

Figure 18A:
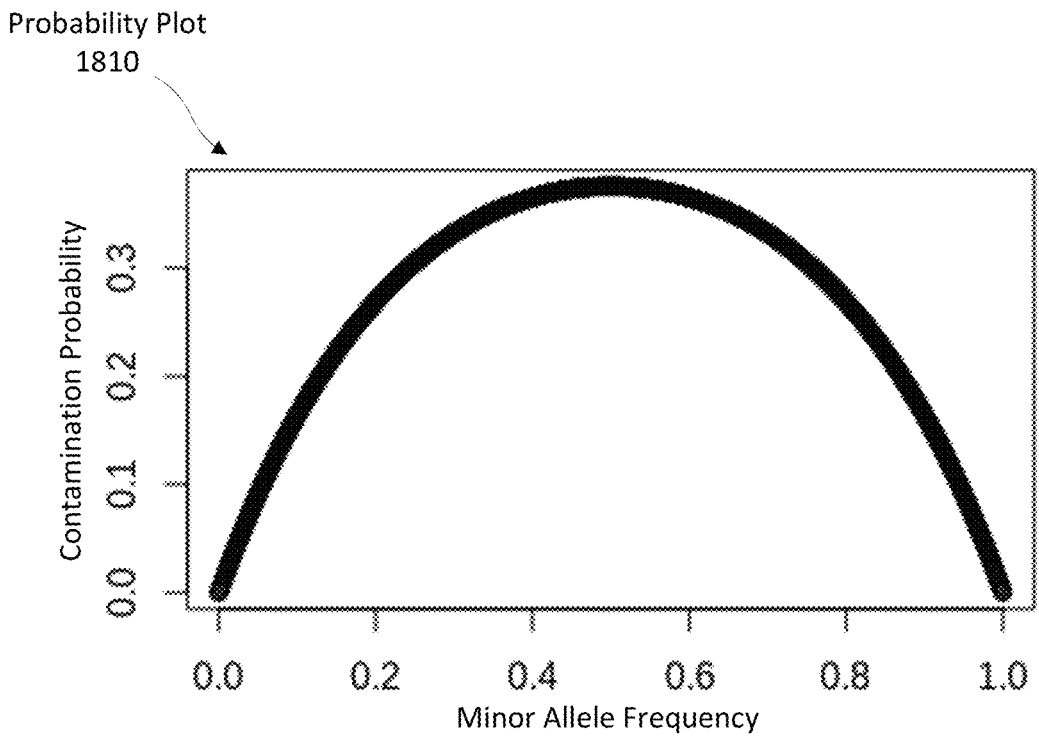
FIGS. 18A-18B are probability plots showing the contamination probability based on a minor allele frequency without and with, respectively, knowing the genotype, according to one example embodiment.

The contamination probability C of an SNP i at site k can be calculated without knowledge of the genotype of the SNP i or, in some embodiments, based on the genotype of the SNP i. For example, FIG. 18A is a probability plot 1810 illustrating the contamination probability C of an SNP i calculated without knowing the host genotype. The contamination probability is highest when MAF is about 50%, and low when MAF is close to 0% or 100%.

Figure 18B:
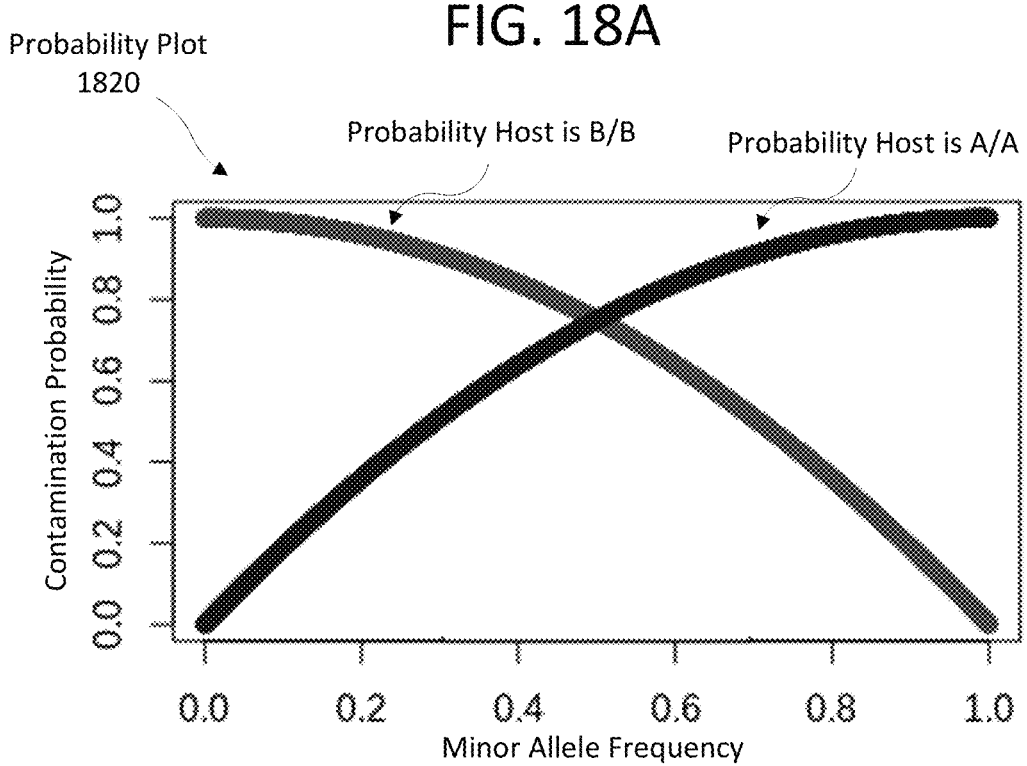

FIG. 18B is a probability plot 1820 illustrating the contamination probability C of an SNP i calculated based on the host genotype. In general, the chance of an SNP i of the source in a test sample being homozygous for a lower frequency allele is relatively low. For example, when the minor allele frequency MAF is low or high. However, if the SNP i is homozygous, the probability of observing an alternate homozygous allele from a contaminant is high. Therefore, this probability relationship can be used to determine the contamination probability of a SNP based on host genotype. The contamination probability C of an SNP i can be used for regression analysis to detect a contamination event. In some embodiments, the contamination probability C can be represented by the equations where the probability of the contaminant genotype being different from the test sample genotype (when test sample is homozygous) can be calculated as follows:

$$P(Cont.!=B/B|Source=B/B)=1-P(B)^2 \quad (9)$$

$$P(Cont.!=A/A|Source=B/B)=1-P(A)^2=1-(1-P(B))^2 \quad (10)$$

where P represents a probability function, Cont. is the contaminant in a test sample, Source is the source in a test sample, B a homozygous alternative allele, and A is a homozygous reference allele.

Figure 19:
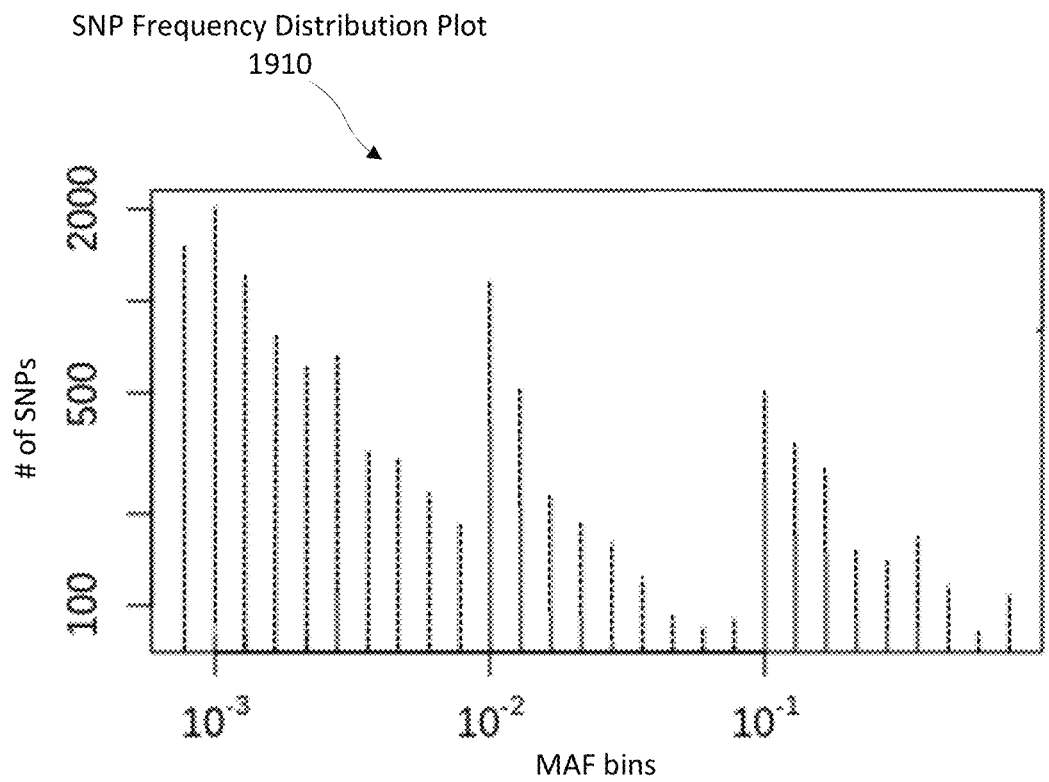
FIG. 19 is a SNP frequency distribution plot showing the number of SNPs in various minor allele frequency bins for a test sample.

Contamination detection workflow 400 using contamination probability C and noise model N was evaluated using two SNP sets with a total n of 14892 SNPs. FIG. 19 is a SNP frequency distribution plot 1910 showing a number of SNPs for each frequency bin for the 14892 SNPs. Here, each bar along the x-axis represents a bin of minor allele frequencies (e.g., MAF bins) for SNPs of a population and the y-axis are the number of SNPs in that frequency bin. The illustrated SNP sets include SNPs from a second SNP set (dashed lines) and a first SNP set (solid lines). The minor allele frequencies MAF for these SNP sets range from about 10-3 to about 1. In this example, a large number of the SNPs in the SNP sets are in the lower frequency range. Table 6 includes a summary of two SNP sets. The SNPs per sample are the SNP genotypes that can be readily called during analysis.

TABLE 6

Summary of SNP sets

|  | Second | First |
|---|---|---|
| Total SNPs | 12174 | 2718 |
| SNPs per sample | 1328 | 629 |
| Median MAF | 0.5% | 1% |

Three modes of contamination detection workflow 400 using a probability model were tested for specificity and sensitivity in detecting contamination: a contamination detection workflow with a weighted linear regression where outliers are removed (herein referred to as "rlmw"), a contamination detection workflow with a weighted linear regression where the weights are designated (herein referred to as "lmw"), and a linear regression (herein referred to as "lm"). In rlmw, outliers are removed using an iterative approach. That is, after each fit of the data, outliers are removed and the fitting process is repeated until a convergence is reached.

Figure 20:
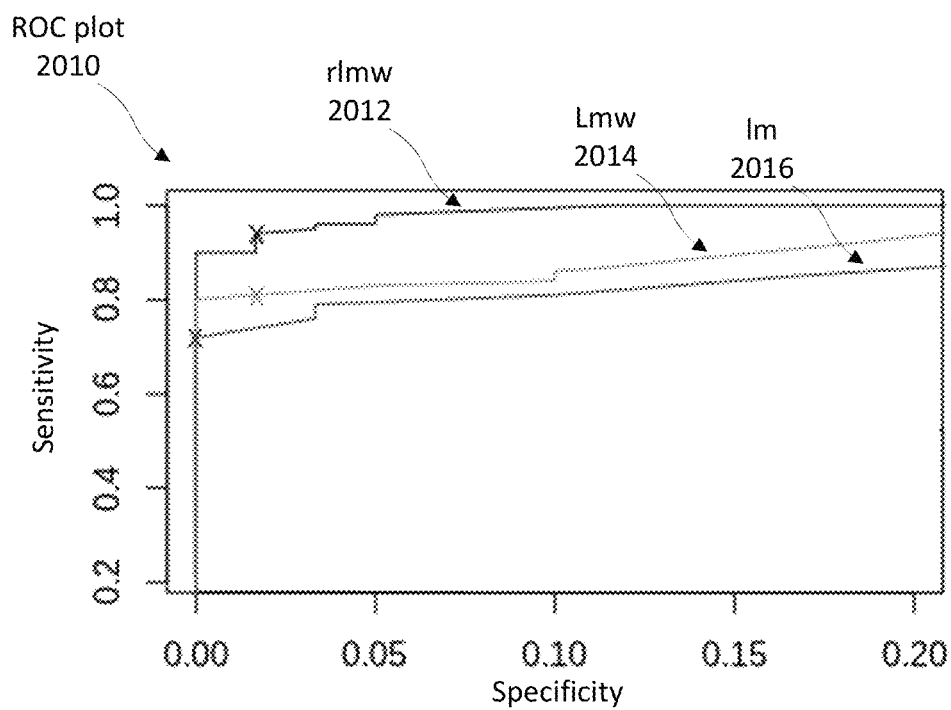
FIG. 20 is a ROC plot for a contamination detection workflow using three different probability models, according to one example embodiment.

FIG. 20 is a ROC plot 2010 showing ROC curves generated during contamination detection workflow 400 using the three probability models. A noise model N was built using 23 individual samples. A reference dataset of n=60 uncontaminated samples was used as true negatives and 100 Poisson simulations between 2 random healthy samples (10 cases each between 0.1% to 1% titrations) were used as true positives. The contamination event threshold was determined as the lowest value with >98% specificity. The minimum contamination fraction was set as 0.0005. In this example, rlmw 2012 performed the best relative to lmw 2014 and lm line 2016.

Figure 21:
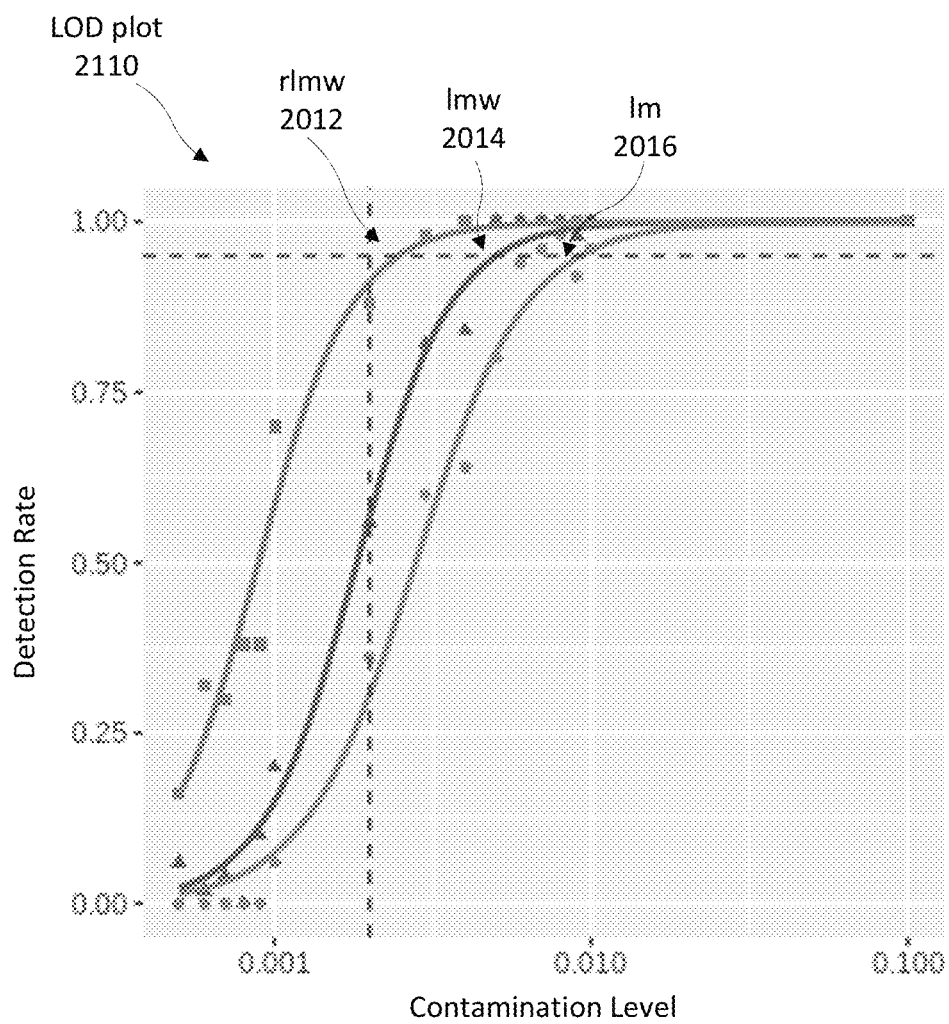
FIG. 21 is a limit of detection plot for a contamination detection workflow using three different probability models, according to one example embodiment.

To determine the limit of detection (LOD) of the contamination detection workflow 400 based on contamination probability (e.g., method 1700) and noise, n=50 Poisson simulations between 2 samples (randomly selected from a pool of healthy samples) were analyzed. FIG. 21 is a limit of detection (LOD) plot 2110 showing the limit of contamination detection obtained using the contamination detection workflow 400 based on contamination probability (e.g., method 1700) and noise using the three probability models rlmw, lmw, and lm. Here, the x-axis is the contamination level and the y axis is the detection rate. Each point on plot 2110 represents the call rate for the n=50 simulations. The crossed dashed lines indicate a target detection of 0.2% contamination level. The data show that the LOD for >95% of cases is a contamination level of about 0.3% for rlmw. Specificity for rlmw at this contamination level is >98%. lmw and lm probability models did not achieve the limit of detection obtained using the rlmw probability model. For example, lm detects about 30% of cases at 0.2% contamination level and about 60% of cases at 0.3% contamination level.

Figure 22A:
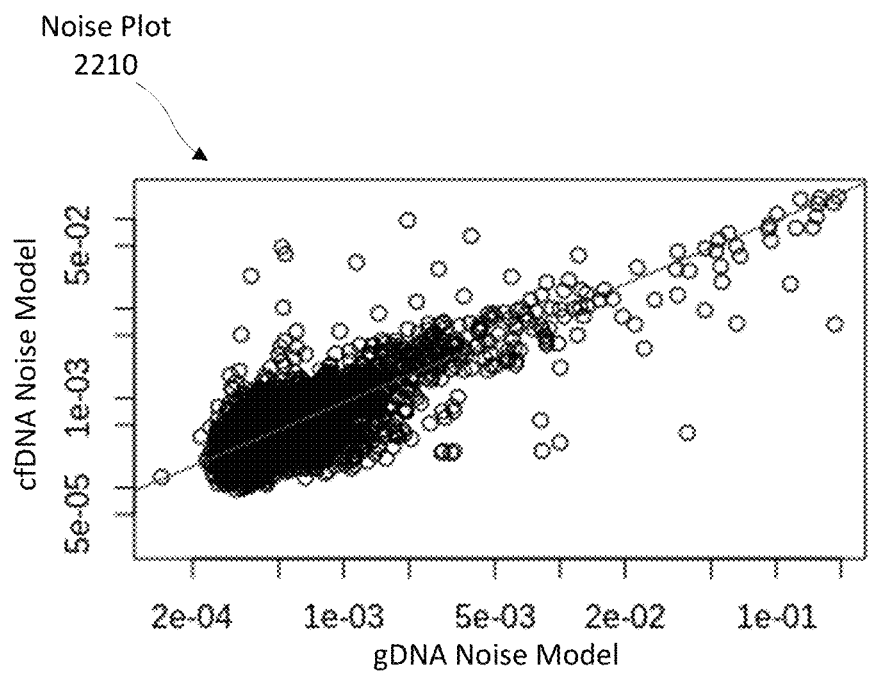
FIG. 22A-22C are noise plots comparing background noise models using three different types of cancer samples to generate the noise models, according to one example embodiment.
Figure 22B:
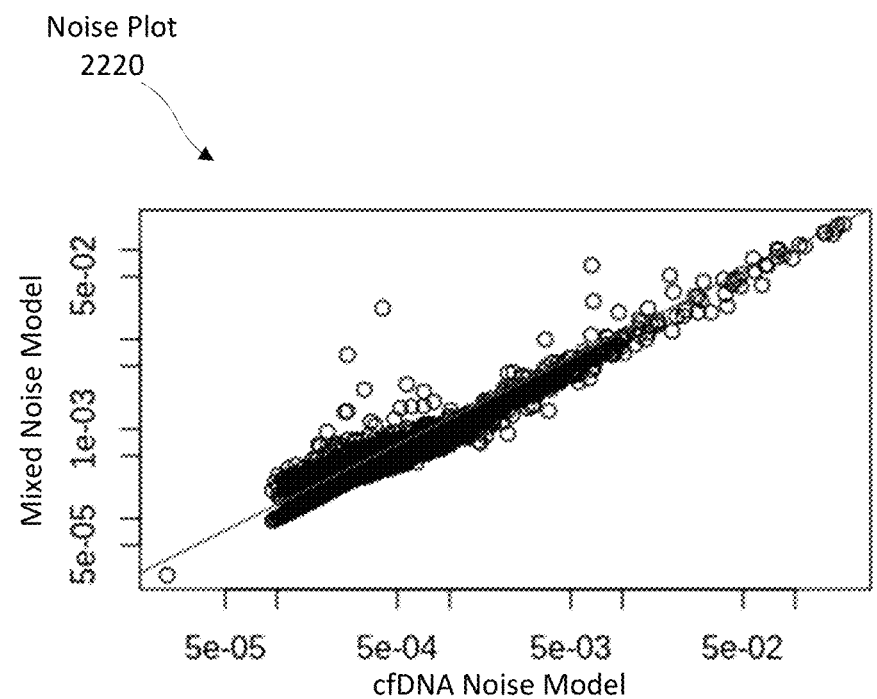
Figure 22C:
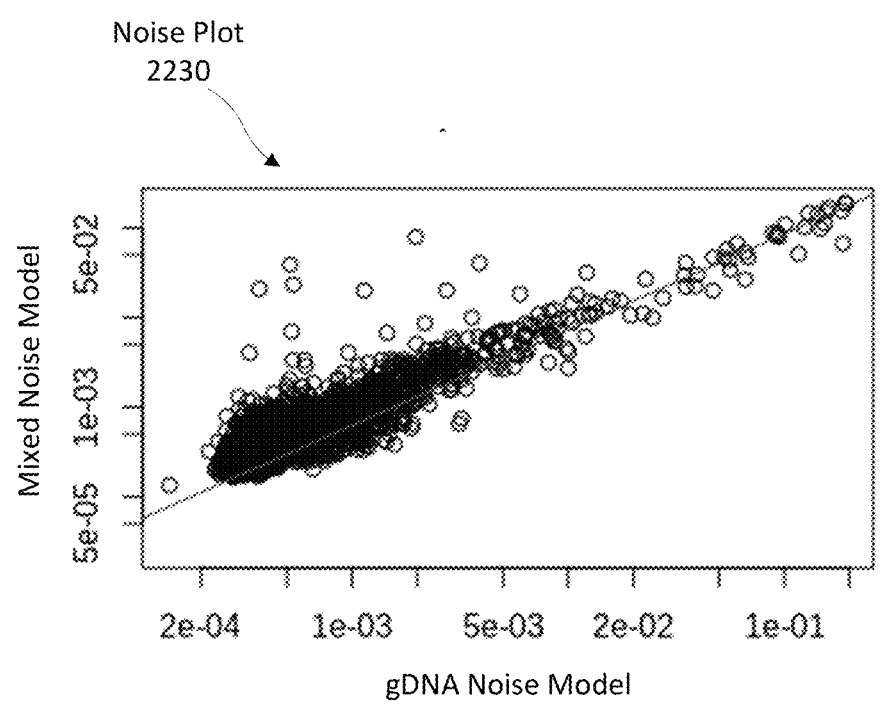

FIG. 22A-22C show noise plots 2210, 2220, 2230, respectively, comparing noise models N built using different sets of variants (such as, for example, $N(VAF_B)$). The sets of variants include genomic DNA (gDNA), cell-free DNA (cfDNA), and a mixture of gDNA and cfDNA samples, respectively. The gDNA noise model was built using n=24 reference cell line samples; the cfDNA noise model was built using n=60 reference individual cfDNA samples; and the mixed noise model was built using n=84 combined gDNA and cfDNA samples. The $R^2$ factor for plot 2210 is 0.73, the $R^2$ factor for plot 2220 is 0.97, and the $R^2$ factor for plot 2310 is 0.90. In this example, the noise models built from gDNA, cfDNA, or a mixture of gDNA and cfDNA are similar. The mixed noise model captures signals from both cfDNA and gDNA.

Figure 23A:
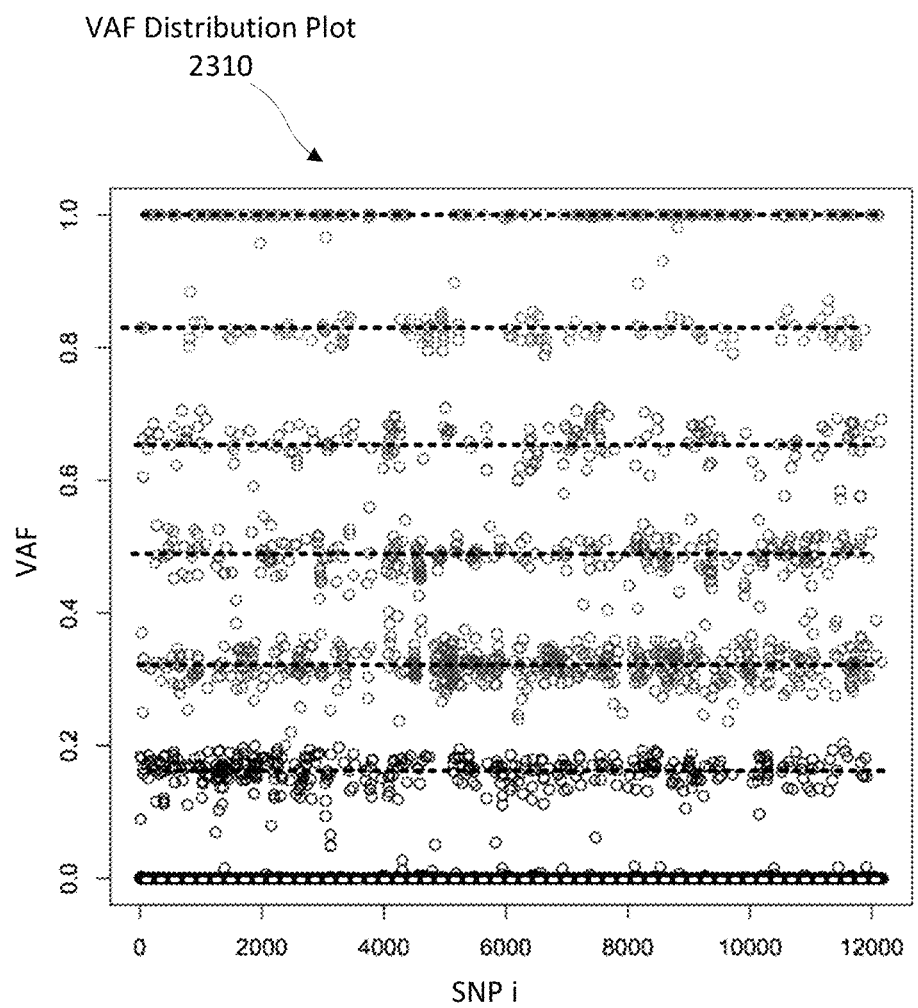
FIG. 23A-23B are variant allele frequency distribution plots for two samples with high contamination levels, according to one example embodiment.
Figure 23B:
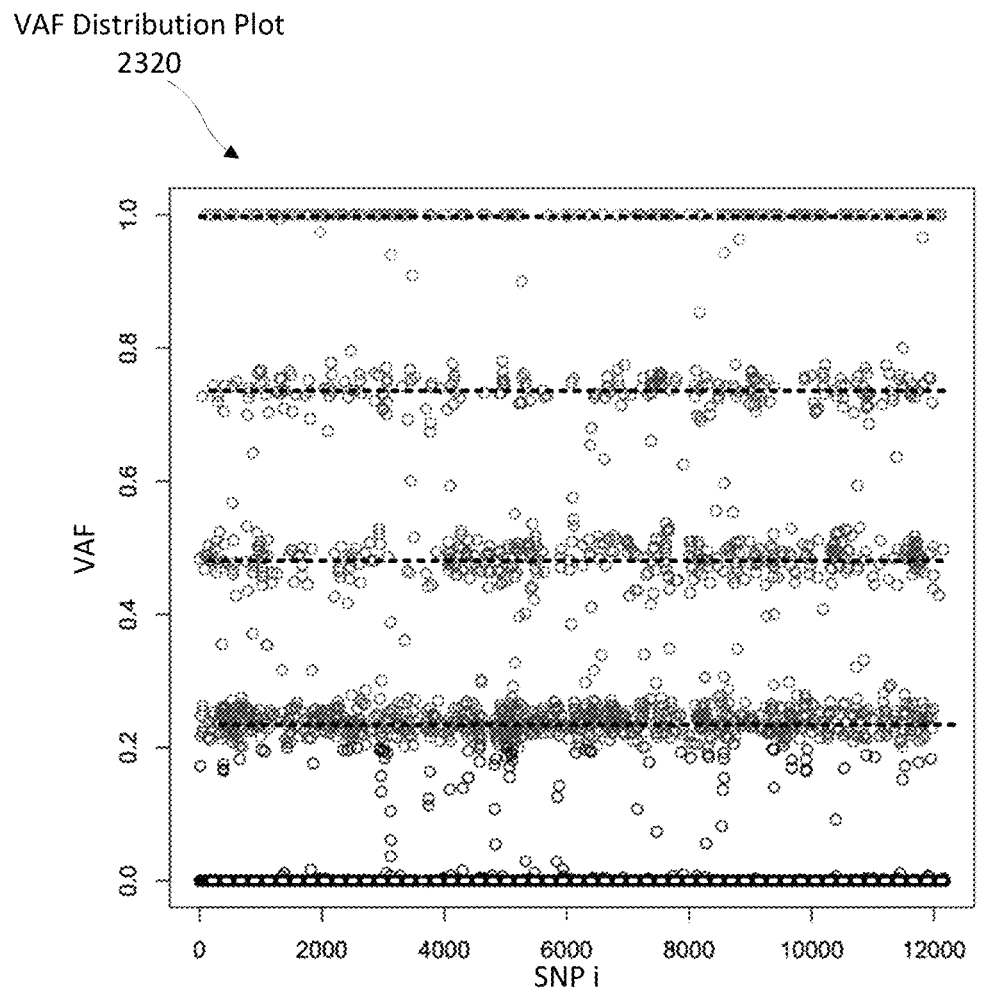

FIGS. 23A and 23B show a VAF distribution plots 2310 and 2320 of the variant allele frequencies for a set of SNPs from a sample with 30% contamination level and a sample with 50% contamination level, respectively. As shown in FIGS. 23A and 23B, the x-axis is the SNP i of the test sample, and the y-x axis is the variant allele frequency VAF. When the source sample and contaminating sample have different genotypes, additional variant allele frequency bands that diverge from the three expected bands. In FIG. 23A, at 30% contamination level seven distinct bands are observed. In. FIG. 23B, at 50% contamination level, only 5 bands are observed with the heterozygous and homozygous contamination bands merged at about 25%. The bands are denoted by dashed lines.

FIGS. 23A and 23B show VAF distribution plots 2310 and 2320, respectively, for a set of SNPs from a sample with 30% contamination level and a sample with 50% contamination level, respectively. As shown in FIGS. 23A and 23B, the x-axis is the SNP i of the test sample, and the y-axis is the variant allele frequency VAF. When the source sample and contaminating sample have different genotypes, additional variant allele frequency bands that diverge from the three expected bands. In FIG. 23A, at 30% contamination level seven distinct bands are observed. In. FIG. 23B, at 50% contamination level, only 5 bands are observed with the heterozygous and homozygous contamination bands merged at about 25%.

Figure 24:
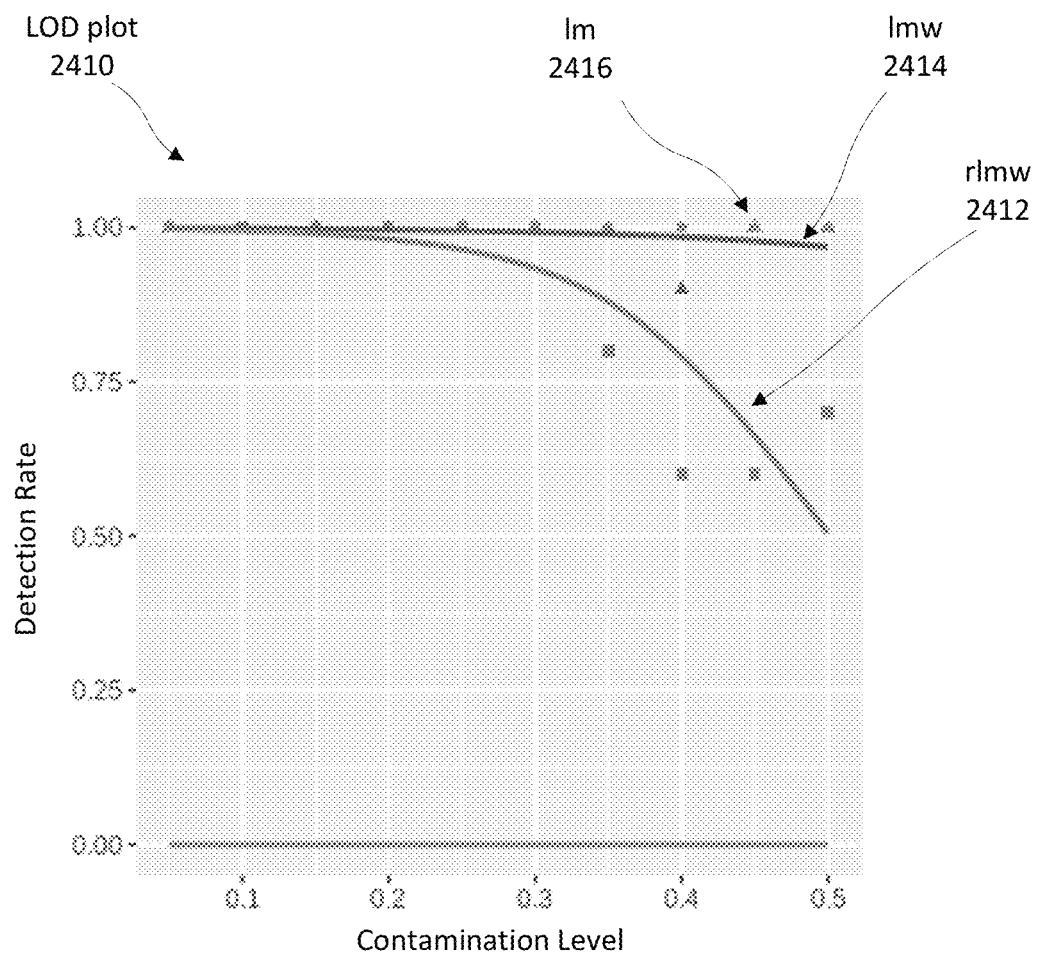
FIG. 24 is a limit of detection plot for a contamination detection workflow using three different probability models, according to one example embodiment.

In some cases, contamination detection workflow 400 can inaccurately determine a contamination event for a high contamination level. To test the LOD for high levels of contamination, n=10 simulations were used for each contamination level of 10, 20, 30, 40, and 50%. FIG. 24 is a LOD plot 2410 showing the detection rate for high levels of contamination obtained using the contamination detection workflow based on probability and noise for the three probability models. Each point on plot 2100 represents the call rate for the n=10 simulations. In this example, rlmw (line 2412) did not perform as well as 1 mw (line 2414) and lm (line 2416). Loss of sensitivity for rlmw, in one example, is due to the removal of outliers.

The kernel density of SNP frequencies can be used to determine a contamination event in test samples with a high contamination level (e.g., 10% or higher). FIG. 25 is a kernel density plot 2510 showing the kernel density estimates of SNP frequencies for an uncontaminated sample. Here, the x-axis is the variant allele frequency and the y-axis is the density. In plot 2510, the uncontaminated sample has 3 SNP peaks. From the kernel density estimate, a threshold for heterozygosity (or a heterozygote window, denoted by the two lines at 0.2 and 0.8 VAF) can be determined. In this example, the heterozygote window (indicated by dashed lines) is from about 0.2 to about 0.8.

Figure 25A:
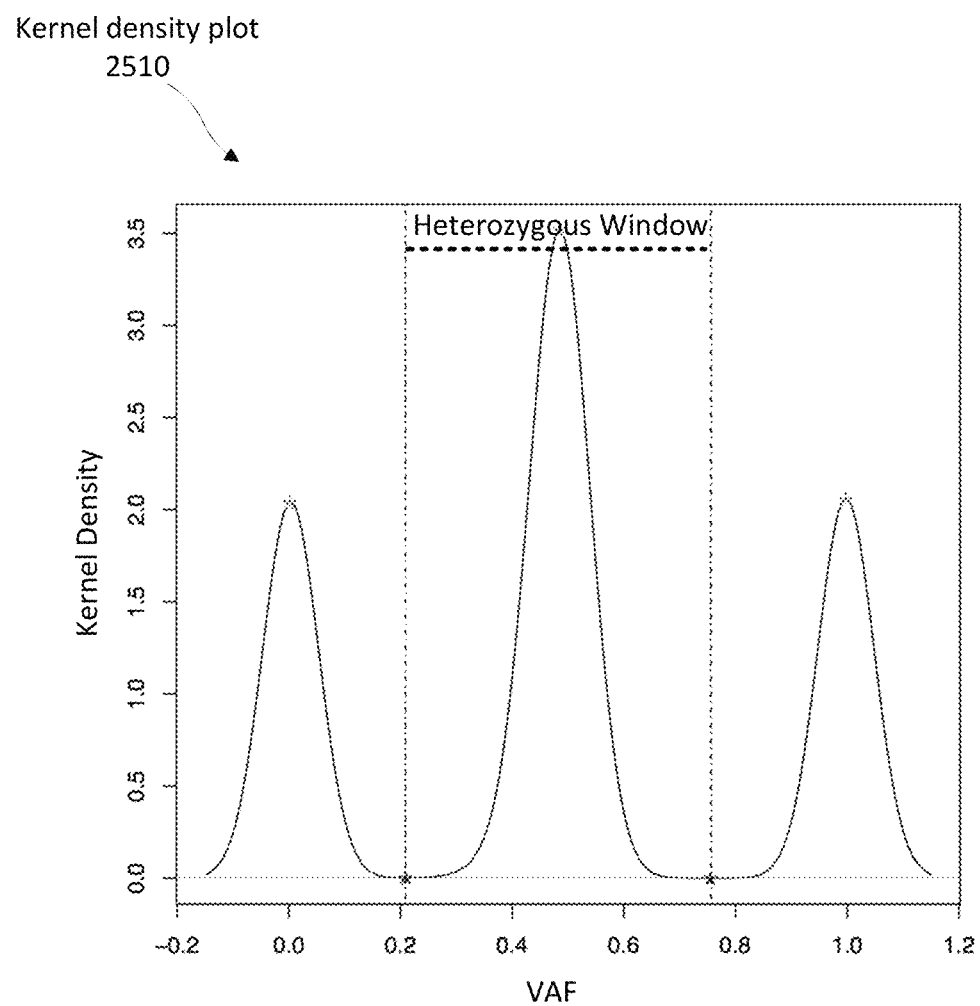
FIGS. 25A-25E are kernel density plots for an uncontaminated test sample, contaminated test samples, and test samples with copy number variations, according to one example embodiment.
Figure 25B:
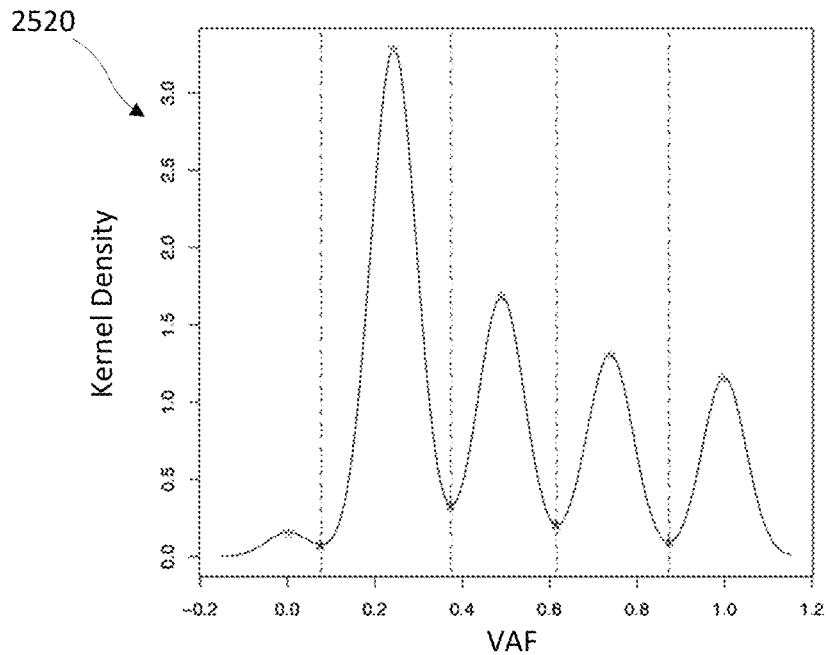
Figure 25C:
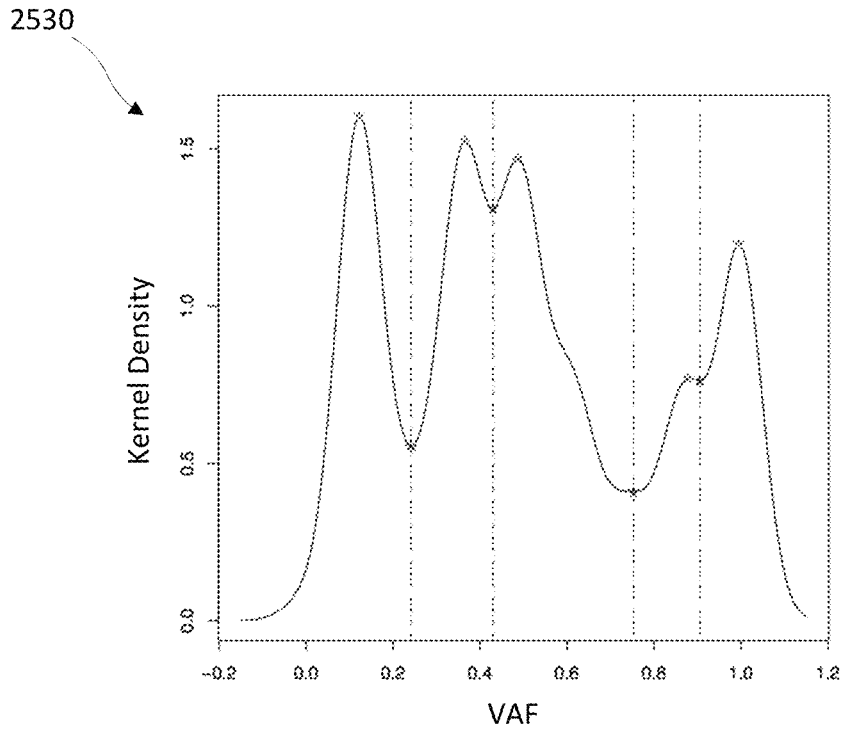

FIGS. 25B and 25C illustrate a kernel density plots 2520 and 2530, respectively for two contaminated samples. For both contaminated samples, the number of SNP peaks is increased relative to the kernel density of the uncontaminated sample in plot 2510 of FIG. 25A.

Figure 25D:
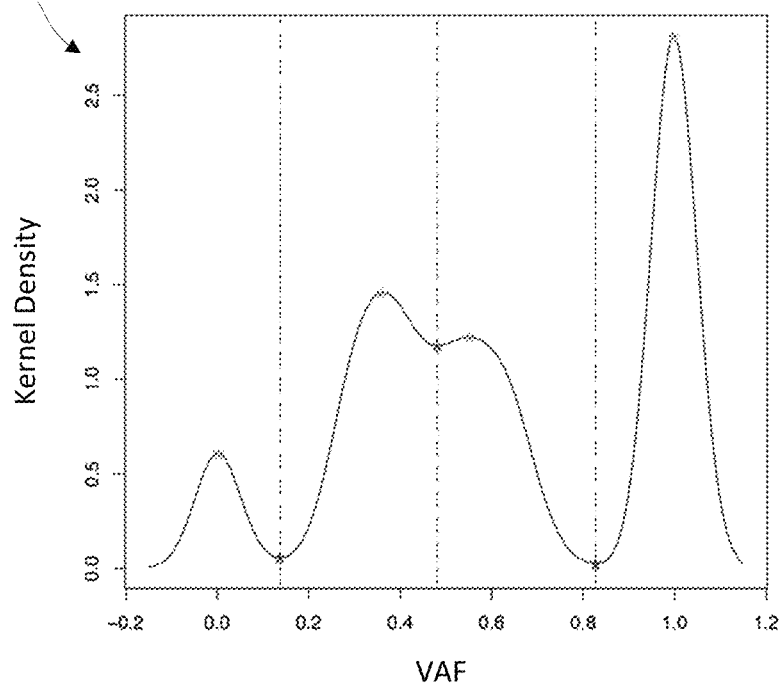
Figure 25E:
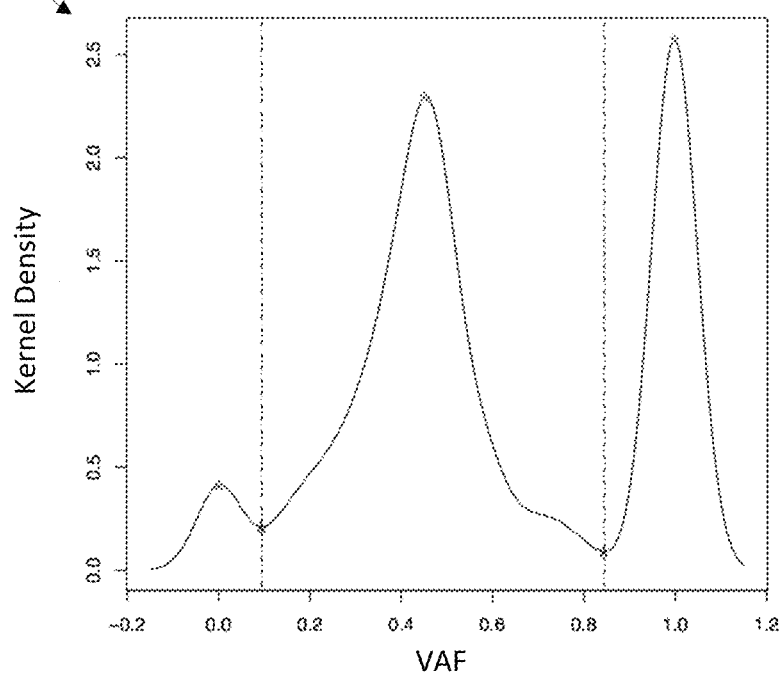

FIGS. 25D and 25E show kernel density plots 2540 and 2550 for two uncontaminated samples that include copy number variations. As shown in FIGS. 25D and 25E, uncontaminated samples that include CNVs also create SNP bands around heterozygous SNPs generally due to the loss of heterozygosity.

Figure 26A:
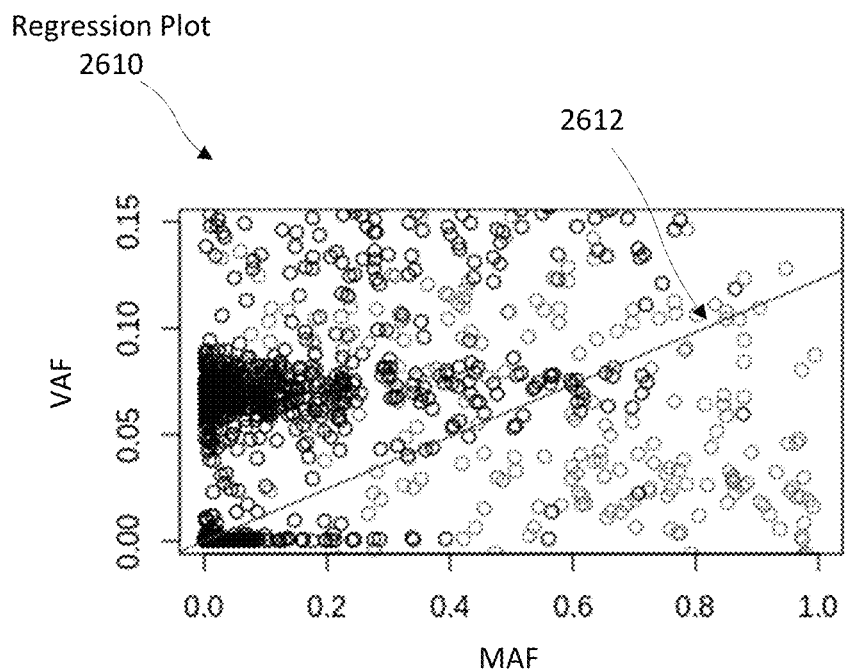
FIG. 26A is a regression plot for a regression plot for a test sample using k clustering, according to one example embodiment.

In another example embodiment, the contamination level can be estimated using the slope of a regression line or K-means clustering. FIG. 26A is a regression plot 2610 of the variant allele frequencies VAF for a test sample against the population MAF. Here, the y-axis is the variant allele frequency and the x-axis is minor allele frequency for each SNP of the test sample. In this example, plot 2610 shows a regression line 2612 determined for the data set that can be used to estimate the contamination level in the test sample.

Figure 26B:
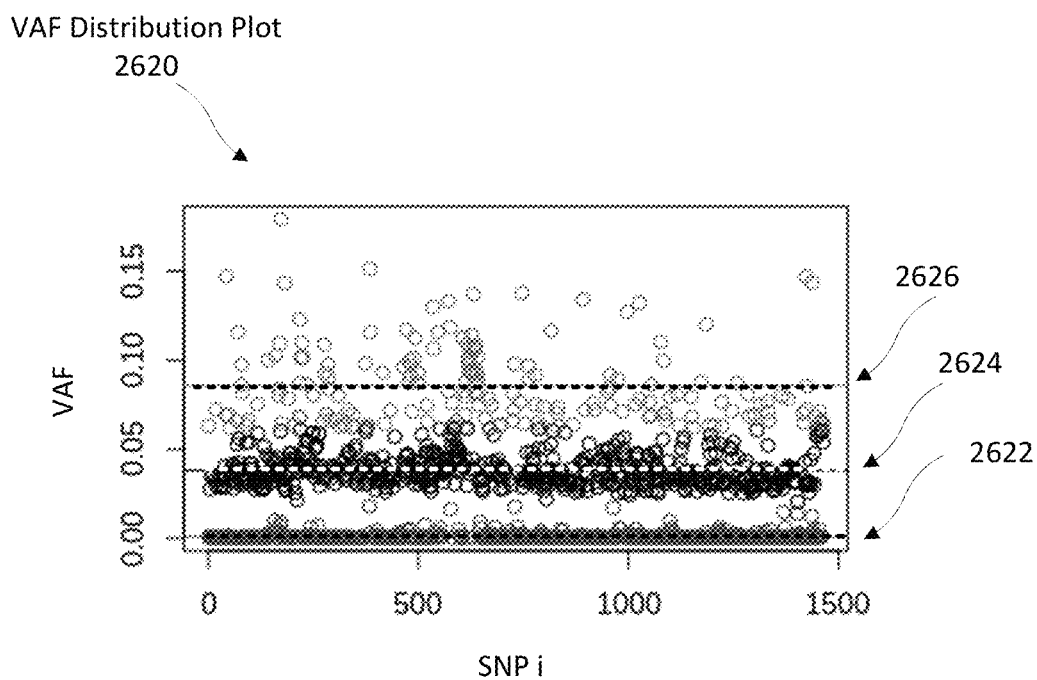
FIG. 26B is a VAF distribution plot for a test sample including k clustering, according to one example embodiment.
Figure 27A:
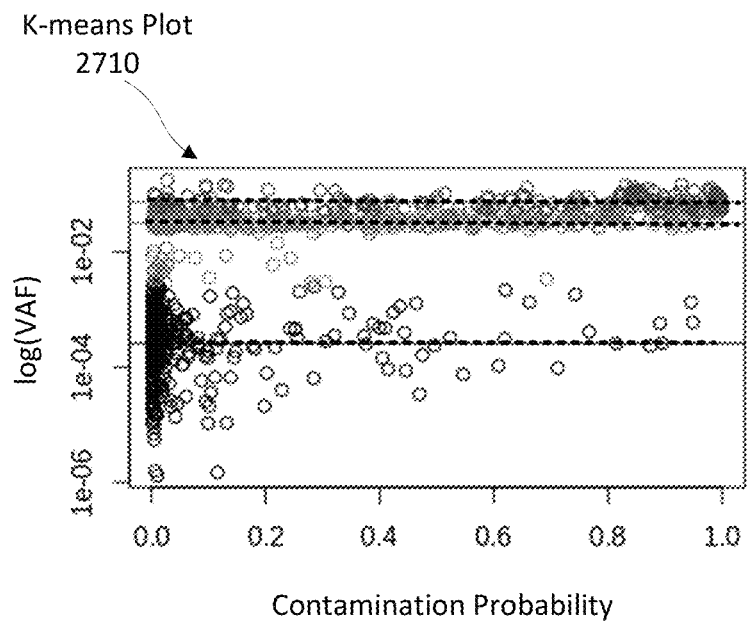
FIG. 27A-27D are K-means plots for test samples with different contamination levels, according to one example embodiment.
Figure 27B:
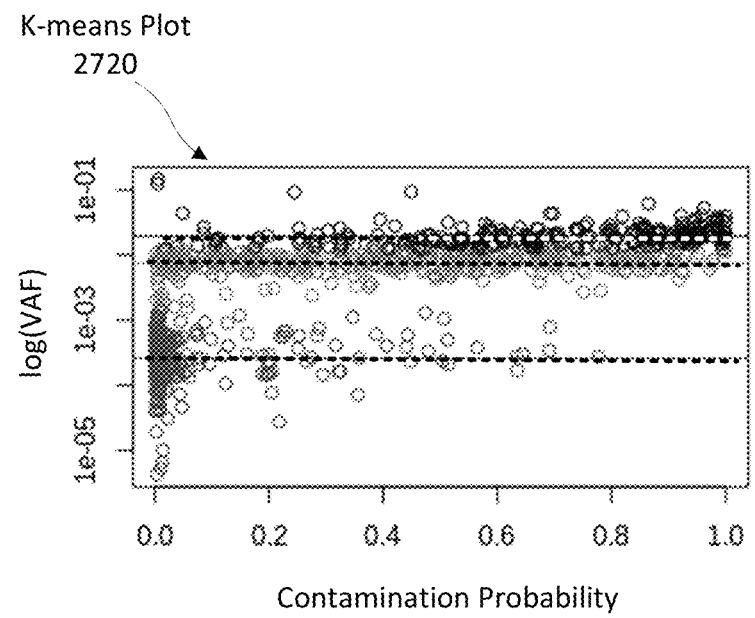
Figure 27C:
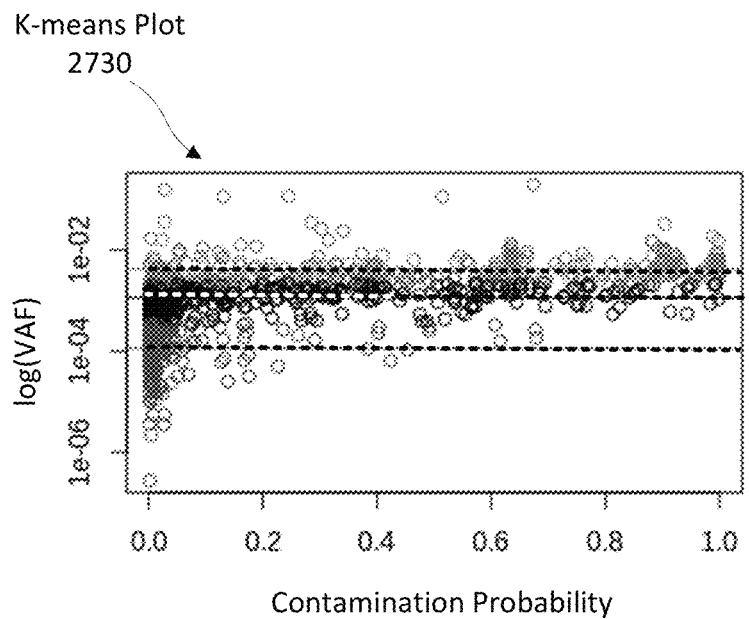
Figure 27D:
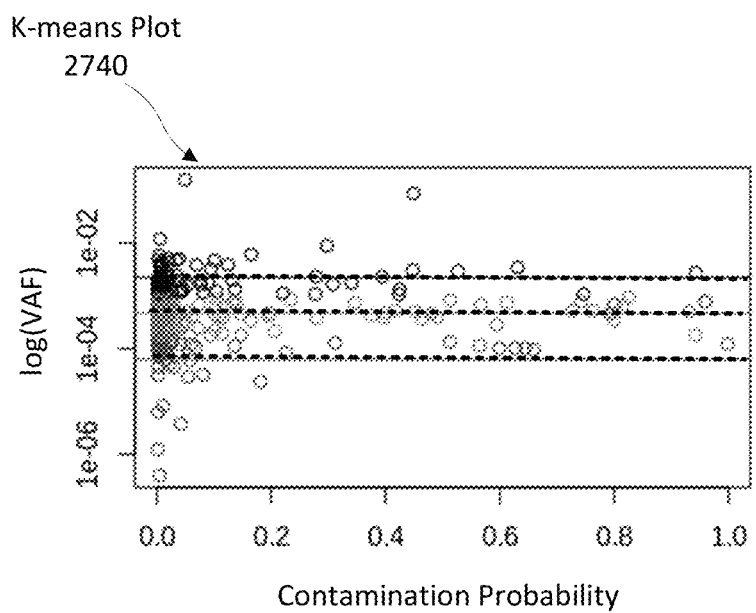

FIG. 26B is a VAF distribution plot 2620 for a test sample partitioned into three clusters (i.e., k=3, with each cluster denoted by a dashed line). Here, the y-axis is the variant allele frequency VAF and the x-axis is the each SNP i of the test sample. These three clusters represent the noise 2622, heterozygous alleles from the contaminant 2624, and homozygous alleles from the contaminant 2626.

FIG. 27A-27D are K-means plots 2710, 2720, 2730, and 2740, respectively, for four different test samples with different contamination levels. Here, the y axis is the logarithm of the variant allele frequency VAF and x-axis is the contamination probability for a set of SNPs for each test sample. The four samples include contamination levels of 10, 5, 1, and 0.5%, respectively. Using a logarithm of the variant allele frequency provides a ready means to distinguish lower levels of contamination because it generates better separation off the variant allele frequency signals.

Contamination detection workflow using a probability model and noise (i.e., method 1700) provides for better limits of detection at both the low end (0.3% contamination) and the high end (up to 50% contamination) compared to the contamination workflow using a linear mode and noise (i.e., method 500).

V. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer-readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for identifying contamination in a test sequence using a processor, the method comprising:
accessing one or more physical samples from a first subject including one or more test sequences that are indicative of a cancer presence;
sequencing the one or more physical samples using a next-generation sequencing machine to produce a plurality of test sequences each comprising at least one single nucleotide polymorphism (SNP) from the first subject and collectively forming an initial population;

calling a plurality of variant alleles in the plurality of test sequences, each called variant allele identified as a SNP across the plurality of test sequences having a variant allele frequency: (VAF) indicating contamination of the initial population with test sequences from a second subject;

identifying a plurality of population minor allele frequencies (MAFs) for the plurality of test sequences, each population minor allele frequency (MAF) quantifying a MAF for a SNP at a test site of a plurality of test sites across the plurality of test sequences;

filtering at least some of the SNPs of the plurality of test sequences in the initial population to form a filtered population, the filtering comprising, for each test sequence of the plurality of test sequences in the initial population:
 selecting SNPs having a VAF in either a first range or a second range, both ranges indicative of homozygosity, and the first range different from the second range,
 for each selected SNP in test sequences whose identified VAF is in the first range, setting a MAF for the selected SNP to the population MAF corresponding to the site of the selected SNP, and
 for each selected SNP in test sequences whose identified VAF is in the second range, setting a MAF for the selected SNP to a quantity one minus the population MAF corresponding to the site of the selected SNP;

generating a noise model that estimates a measure of background noise level present in the plurality of test sequences in the filtered population based on measures of background noise levels present in a plurality of test sequences indicative of healthy individuals;

applying a contamination model to a test sequence of the plurality of test sequences in the filtered population using the identified plurality of population MAFs of the plurality of test sequences, the identified VAFs for SNPs across the plurality of test sequences, and the generated noise model based on the plurality of test sequences indicative of healthy individuals to obtain a confidence score representing a likelihood the test sequence originates from the second subject and is contaminating the initial population, wherein the confidence score is below a threshold, indicating the test sequence originates from the second subject; and responsive to the confidence score indicating the test sequence originates from the second subject, discarding the one or more physical samples due to contamination.

2. The method of claim 1, wherein the contamination model models each range of homozygous SNPs independently.

3. The method of claim 1, wherein applying the contamination model further comprises:
 regressing the identified VAFs for SNPs of the test sequence of the plurality of test sequences in the filtered population against the noise model and a population MAF of the plurality of population MAFs to determine a p-value of a regression coefficient associated with the population MAF.

4. The method of claim 3, wherein the confidence score is based on the p-value of the regression coefficient.

5. The method of claim 1, wherein filtering at least some of the plurality of test sequences to form the filtered population further comprises at least one of, for each test sequence of the plurality of test sequences, removing heterozygous SNPs with a VAF in a range between 0.2 and 0.8.

6. The method of claim 1, wherein filtering at least some of the plurality of test sequences to form the filtered population further comprises at least one of, for each test sequence of the plurality of test sequences:
 removing SNPs including no-calls; and
 removing SNPs with a depth less than 1000.

7. The method of claim 1, wherein the measure of background noise level is a population measure of allele frequency in the plurality of test sequences indicative of healthy individuals.

8. The method of claim 1, wherein generating the noise model further comprises identifying a background noise that represents static noise generated when sequencing a SNP.

9. The method of claim 1, wherein generating the noise model further comprises:
 determining a noise coefficient for each SNP in the plurality of test sequences indicative of healthy individuals, the noise coefficient predicting the expected noise level for each SNP.

10. The method of claim 1 wherein the generated noise model is additionally based on a sample type of the plurality of test sequences indicative of healthy individuals.

11. The method of claim 1, wherein the contamination model additionally includes a random error term.

12. The method of claim 1, wherein the first range is less than the second range.

13. The method of claim 1, wherein the first range is between 0.0 and 0.2 and the second range is between 0.8 and 1.0.

14. The method of claim 1, wherein the first range is below a first cutoff value and the second range is above a second cutoff value.

* * * * *